United States Patent
Vejborg et al.

(10) Patent No.: US 12,060,542 B2
(45) Date of Patent: Aug. 13, 2024

(54) POLYPEPTIDES AND COMPOSITIONS COMPRISING SUCH POLYPEPTIDES

(71) Applicant: Novozymes A/S, Bagsvaerd (DK)

(72) Inventors: Rebecca Munk Vejborg, Allerod (DK); Dorotea Raventos Segura, Rungsted (DK); Jesper Salomon, Holte (DK); Johanne M. Jensen, Brighton (AU); Rune Nygaard Monrad, Hillerod (DK); Anne Vindum Due, Bagsvaerd (DK); Martin Gudmand, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 18/348,277

(22) Filed: Jul. 6, 2023

(65) Prior Publication Data
US 2024/0010955 A1   Jan. 11, 2024

Related U.S. Application Data

(62) Division of application No. 16/759,635, filed as application No. PCT/EP2018/079853 on Oct. 31, 2018, now Pat. No. 11,767,492.

(30) Foreign Application Priority Data

Nov. 1, 2017  (EP) .................................... 17199594

(51) Int. Cl.
  *C11D 3/386*    (2006.01)
  *C11D 3/20*     (2006.01)
  *C11D 17/00*    (2006.01)
  *C12N 9/24*     (2006.01)

(52) U.S. Cl.
  CPC ........ *C11D 3/38636* (2013.01); *C11D 3/2065* (2013.01); *C11D 3/38609* (2013.01); *C11D 3/38627* (2013.01); *C11D 3/38645* (2013.01); *C11D 3/38672* (2013.01); *C11D 17/0039* (2013.01); *C12N 9/2402* (2013.01); *C12Y 302/01052* (2013.01); *C11D 2111/12* (2024.01)

(58) Field of Classification Search
  None
  See application file for complete search history.

(56) References Cited

U.S. PATENT DOCUMENTS 6,465,410 B1   10/2002   Gamble

FOREIGN PATENT DOCUMENTS

| CN | 1051299 A | 5/1991 |
|---|---|---|
| CN | 1321168 A | 11/2001 |
| EP | 425019 A1 | 5/1991 |
| EP | 2302031 A1 | 3/2011 |
| IN | 201847043765 | 12/2018 |
| IN | 201847043766 | 12/2018 |
| IN | 201847048708 | 1/2019 |
| IN | 201947044752 | 11/2019 |
| JP | 2005247981 A | 9/2005 |
| WO | 98/50512 A1 | 11/1998 |
| WO | 99/57155 A1 | 11/1999 |
| WO | 2004/061117 A2 | 7/2004 |
| WO | 2008/043175 A1 | 4/2008 |
| WO | 2008/157350 A2 | 12/2008 |
| WO | 2014/110675 A1 | 7/2014 |
| WO | 2015/185689 A1 | 12/2015 |
| WO | 2016/176240 A1 | 11/2016 |
| WO | 2017/186937 A1 | 11/2017 |
| WO | 2017/186943 A1 | 11/2017 |
| WO | 2017/207770 A1 | 12/2017 |
| WO | 2018/184873 A1 | 10/2018 |
| WO | 2020/002608 A1 | 1/2020 |

OTHER PUBLICATIONS

GenBank Database Accession No. SNU89609, "beta-N-acetylhexosaminidase [*Streptococcus merionis*]", Aug. 15, 2017, 1 page (Year: 2017).*
Little et al., "Modification and periplasmic translocation of the biofilm exopolysaccharide poly-β-1,6-N-acetyl-D-glucosamine", PNAS 111:11013-11018, 2014 (Year: 2014).*
Claesson et al., 2007, FEMS Microbiol. Lett., vol. 269, pp. 22-28.
Flemming et al., 2010, Nature Reviews Microbiology, vol. 8, pp. 623-633.
Kim et al., 2015, GenBank Accession No. AKP66020.
Li et al., 2013, UniProt Accession No. U2W2U5.
Sun et al., 2016, EBI Accession No. A0A0R1FZT1.
Sun et al., 2015, GenBank Accession No. KRL51886.
Tamarit et al., 2015, EBI Accession No. A0A0M9D3N9.
Wilson et al., 2000, J. Mol. Biol., vol. 297, pp. 233-249.
Yu et al., 2015, Cell Research, vol. 25, pp. 1352-1367.
Anonymous, 2017, EBI Accession No. A0A239SWH9.

* cited by examiner

*Primary Examiner* — David Steadman
(74) *Attorney, Agent, or Firm* — Elias Lambiris

(57) ABSTRACT

The present invention relates to compositions such as cleaning compositions comprising enzymes. The invention further relates to the use of the compositions comprising such enzymes in cleaning processes.

19 Claims, 2 Drawing Sheets
Specification includes a Sequence Listing.

POLYPEPTIDES AND COMPOSITIONS COMPRISING SUCH POLYPEPTIDES

CROSS-REFERENCE TO RELATED APPLICATIONS

This application is a divisional of U.S. application Ser. No. 16/759,635 filed Apr. 27, 2020, now pending, which is a 35 U.S.C. 371 national application of international application no. PCT/EP2018/079853 filed Oct. 31, 2018, which claims priority or the benefit under 35 U.S.C. 119 of European application no. 17199594.7 filed Nov. 1, 2017. The disclosure of each application is fully incorporated herein by reference.

REFERENCE TO A SEQUENCE LISTING

This application contains a Sequence Listing in computer readable form, which is incorporated herein by reference. The name of the file containing the Sequence Listing is SQ.xml, which was created on Jul. 6, 2023 and has 42,732 bytes.

BACKGROUND OF THE INVENTION

The present invention relates to compositions such as cleaning compositions comprising enzymes having hexosaminidase activity such as dispersins obtained from *Lactobacillus* or *Streptococcus*. The invention further relates to methods and use of compositions comprising such enzymes in cleaning processes, e.g., for stain removal.

DESCRIPTION OF THE RELATED ART

Enzymes have been used in detergents for decades. Usually, a cocktail of various enzymes is added to detergent compositions. The enzyme cocktail often comprises various enzymes, wherein each enzyme targets a specific substrate, e.g., amylases are active towards starch stains, proteases on protein stains and so forth. Textiles surface and hard surfaces, such as dishes or the inner space of a laundry machine enduring a number of wash cycles, become soiled with many different types of soiling which may compose of proteins, grease, starch etc. One type of stain may compose of organic matter, such as cell debris, biofilm, EPS, etc. Polypeptides having hexosaminidase activity include Dispersins such as Dispersin B (DspB), which are described as β-N-acetylglucosaminidases belonging to the Glycoside Hydrolase 20 family. WO 2004/061117 (Kane Biotech) describes the use of compositions comprising DspB for reducing and preventing biofilm caused by poly-N-acetylglucosamine-producing bacteria and Kane et al. describes the use of compositions comprising dispersins for reducing biofilm on medical devises and for wound care. WO 98/50512 (Procter and Gamble) discloses laundry or cleaning products comprising one or more hexosaminidase enzymes. The present invention provides suitable enzymes for use in detergents and for deep cleaning of items during laundry and cleaning process.

SUMMARY OF THE INVENTION

A first aspect of the invention relates to a composition comprising a *Lactobacillus* or *Streptococcus* hexosaminidase, wherein the composition further comprises:
(a)
  i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
  ii. optionally, one or more enzymes, preferably selected from proteases, amylases or lipases,
  iii. optionally one or more surfactants, preferably selected from anionic and nonionic surfactants,
  iv. optionally one or more polymers;
or
(b) a granule comprising
  i. a core comprising a *Lactobacillus* or *Streptococcus* hexosaminidase and optionally,
  ii. a coating consisting of one or more layer(s) surrounding the core.

The hexosaminidase preferably has N-acetylglucosaminidase activity, preferably β-1,6 N-acetylglucosaminidase activity.

The present invention relates to a cleaning composition comprising at least 0.01 mg *Lactobacillus* hexosaminidase and a cleaning component, wherein the cleaning component is
(a) at least one surfactant;
(b) at least one builder; or
(c) at least one polymer.

The invention further relates to the use of a composition according to the invention for cleaning of an item, wherein the item is a textile or a surface.

The invention further relates to the use of a composition according to the invention, preferably a cleaning composition such as a detergent composition comprising a *Lactobacillus* hexosaminidase,
a) for preventing, reducing or removing stickiness of the item;
b) for pretreating stains on the item;
c) for preventing, reducing or removing redeposition of soil during a wash cycle;
d) for preventing, reducing or removing adherence of soil to the item;
e) for maintaining or improving whiteness of the item;
for preventing, reducing or removing malodor from the item, wherein the item is a textile.

The invention further relates to a method of formulating a cleaning composition comprising adding a *Lactobacillus* hexosaminidase and at least one cleaning component.

The invention relates to a kit intended for cleaning, wherein the kit comprises a solution of an enzyme mixture comprising *Lactobacillus* hexosaminidase, and an additional enzyme selected from proteases, amylases, cellulases and lipases.

The invention further relates to a method of treating a fabric comprising:
(a) contacting the fabric with an aqueous solution of *Lactobacillus* hexosaminidase; and
(b) optionally rinsing and drying the textile.

The invention relates to a method for cleaning or laundering an item comprising the steps of:
(a) exposing an item to a wash liquor comprising a *Lactobacillus* hexosaminidase of the invention or a detergent composition comprising a *Lactobacillus* hexosaminidase;
(b) completing at least one wash cycle; and
(c) optionally rinsing the item, wherein the item is a fabric.

Figure 1:
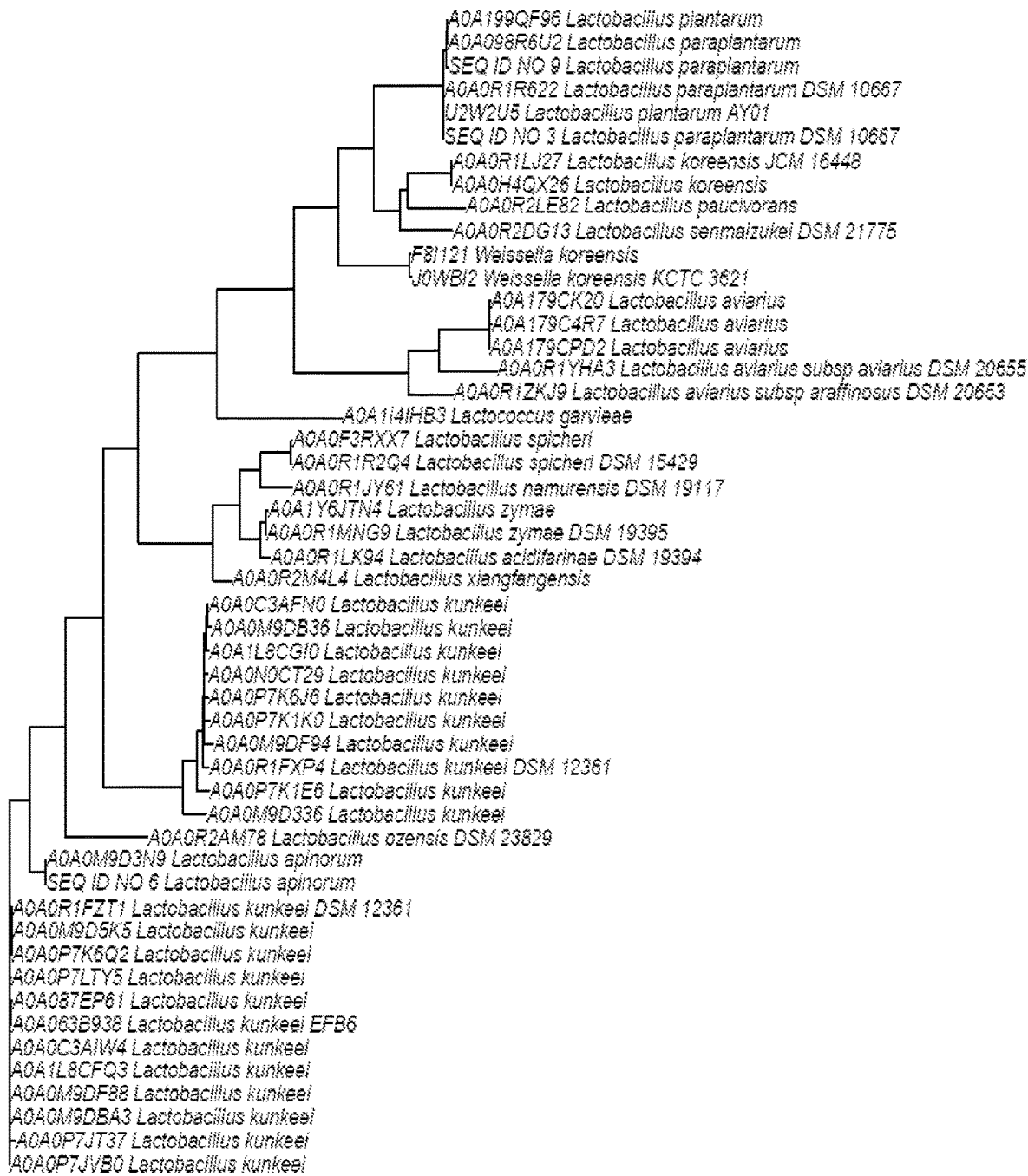
FIG. 1. In one aspect the polypeptides of the invention, e.g., all belong to the *Lactobacillus* clade, which is illustrated as a phylogenetic tree in FIG. 1. The *Lactobacillus* clade or clade of *Lactobacillus* is a group of enzymes all related to the same ancestor and share common properties of taxonomic order Lactobacillales. Polypeptides forming a group within the clade (a subclade) of the phylogenetic tree can also share common properties and are more closely related than other polypeptides in the clade.

Overview of Sequences of the *Lactobacillus* clade
  SEQ ID NO: 1 is the DNA encoding the full-length polypeptide from *Lactobacillus paraplantarum* DSM 10667
  SEQ ID NO: 2 is the polypeptide derived from SEQ ID NO: 1
  SEQ ID NO: 3 is the mature polypeptide of SEQ ID NO: 2
  SEQ ID NO: 4 is the DNA encoding the full-length polypeptide from *Lactobacillus apinorum*
  SEQ ID NO: 5 is the polypeptide derived from SEQ ID NO: 4
  SEQ ID NO: 6 is the mature polypeptide of SEQ ID NO: 5
  SEQ ID NO: 7 is the DNA encoding the full-length polypeptide from *Lactobacillus paraplantarum*
  SEQ ID NO: 8 is the polypeptide derived from SEQ ID NO: 7
  SEQ ID NO: 9 is the mature polypeptide of SEQ ID NO: 8
  SEQ ID NO: 10 is the *Bacillus clausii* secretion signal
  SEQ ID NO: 11 is a His-tag sequence
  SEQ ID NO: 16 is the DNA encoding the full-length polypeptide from *Streptococcus merionis*
  SEQ ID NO: 17 is the polypeptide derived from SEQ ID NO: 16
  SEQ ID NO: 18 is the mature polypeptide of SEQ ID NO: 17.

DETAILED DESCRIPTION OF THE INVENTION

Various enzymes are applied in cleaning processes each targeting specific types of soiling such as protein, starch and grease soiling. Enzymes are standard ingredients in detergents for laundry and dish wash. The effectiveness of these commercial enzymes provides detergents which remove much of the soiling. However, organic stains such as EPS (extracellular polymeric substance) comprised in much biofilm constitute a challenging type of soiling due to the complex nature of such organic matters. EPS is mostly composed of polysaccharides (exopolysaccharides), e.g., PNAG (poly-N-acetylglucosamine) and proteins, but include other macro-molecules such as eDNA, lipids and other organic substances. Organic stains, like biofilm or components hereof, such as PNAG may be sticky or glueing, which when present on textile, may give rise to redeposition or backstaining of soil resulting in a greying of the textile. Further, when dirty laundry items are washed together with less dirty laundry items the dirt present in the wash liquor tend to stick to organic stains, e.g., biofilm or biofilm components as a result, hereof the laundry item is more "soiled" after wash than before wash. This effect may also be termed redeposition. Another drawback of organic stains is the malodor as various malodor related molecules are often associated with organic stains such as biofilm.

The present invention relates to polypeptides, the use, methods and compositions comprising hexosaminidases preferably obtained from the taxonomic order of Lactobacillales, preferably from the genus *Lactobacillus*. The terms "*Lactobacillus* hexosaminidase" and "hexosaminidase obtained from *Lactobacillus*" may be used interchangeably throughout. The present invention further relates to polypeptides the use, methods and compositions comprising hexosaminidases obtained from the taxonomic order of *Streptococcus*. The terms "*Streptococcus* hexosaminidase" and "hexosaminidase obtained from *Streptococcus*" may be used interchangeably throughout.

The hexosaminidases are preferably dispersins and comprise N-acetylglucosaminidase and/or β-1,6-N-acetylglucosamininidase activity.

Polypeptides Having Hexosaminidase Activity

Hexosaminidase: The term "hexosaminidases" means a polypeptide having hexosaminidase activity (hexosaminidases), and includes EC 3.2.1., e.g., that catalyzes the hydrolysis of N-acetyl-D-hexosamine or N-acetyl-glucosamine polymers found, e.g., in biofilm. The term includes dispersins and includes polypeptides having N-acetylglucosaminidase activity and β-1,6 N-acetylglucosaminidase activity. The term "polypeptide having hexosaminidase activity" may be used interchangeably with the term hexosaminidases and similar the term "polypeptide having beta-1,6-N-acetylglucosaminidase activity" may be used interchangeably with the term beta-1,6-N-acetylglucosamininidases. For purposes of the present invention, hexosaminidase activity may be determined according to the procedure described in Assay I or as described in Example 11.

Dispersin: The term "dispersin" and the abbreviations "Dsp" or "Disp" means a polypeptide having hexosaminidase activity, EC 3.2.1.—that catalyzes the hydrolysis of β-1,6-glycosidic linkages of N-acetyl-glucosamine polymers (poly-N-acetylglucosamine, PNAG) found, e.g., in biofilm. Thus, dispersins is an enzyme having beta-1,6 N-acetylglucosaminidase activity.

In a preferred aspect, the polypeptide of the invention is comprised in a specific clade of hexosaminidases. This clade is in the present context termed *Lactobacillus* as the hexosaminidases from the clade are obtained from bacteria within the taxonomic order of Lactobacillales, preferably from the *Lactobacillus* genus. The term *Lactobacillus* hexosaminidase means hexosaminidases obtained from the taxonomic order of Lactobacillales, preferably from the *Lactobacillus* genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. The phylogenetic tree of the *Lactobacillus* clade is shown in FIG. 1. The polypeptides of the invention are preferably obtained from *Lactobacillus paraplantarum* or *Lactobacillus apinorum*.

In another aspect, one polypeptide of the invention is obtained from *Streptococcus*, preferably *Streptococcus merionis*. The term *Streptococcus* hexosaminidase means hexosaminidases obtained from *Streptococcus* genus.

The polypeptides, e.g., those comprised in the *Lactobacillus* clade, find use in cleaning processes and compositions of the invention are listed in the table below. The hexosaminidases of Table 1 have beta-1,6-N-acetylglucosaminidase activity and are thus dispersins. The dispersins of this group have been found to be particularly useful in cleaning of organic stains, e.g., PNAG from textiles. In particular, dispersins of Table 1 may be formulated in compositions, e.g., cleaning compositions, comprising a dispersin obtained from *Lactobacillus* and a detergent adjunct. The polypeptides and compositions of the invention are useful in cleaning processes such as laundry and/or are useful for reduction, removal or preventing biofilm and/or for removing PNAG stains, e.g., from textiles and hard surfaces.

TABLE 1

Hexosaminidase polypeptides having beta-1,6 N-acetylglucosaminidase activity comprised in the *Lactobacillus* clade

| | |
|---|---|
| SEQ ID NO: 3 | *Lactobacillus paraplantarum* DSM 10667 |
| SEQ ID NO: 6 | *Lactobacillus apinorum* |
| SEQ ID NO: 9 | *Lactobacillus paraplantarum* |
| UniProtKB/TrEMBL | Additional dispersins |
| J0WBI2 | *Weissella koreensis* KCTC 3621 |
| A0A0P7K1K0 | *Lactobacillus kunkeei* |
| A0A0P7K6J6 | *Lactobacillus kunkeei* |
| U2W2U5 | *Lactobacillus plantarum* AY01 |
| A0A1L8CGI0 | *Lactobacillus kunkeei* |
| A0A0P7K6Q2 | *Lactobacillus kunkeei* |
| A0A098R6U2 | *Lactobacillus paraplantarum* |
| A0A0P7LTY5 | *Lactobacillus kunkeei* |
| A0A0M9D336 | *Lactobacillus kunkeei* |
| A0A0R1JY61 | *Lactobacillus namurensis* DSM 19117 |
| A0A0C3AIW4 | *Lactobacillus kunkeei* |
| A0A0M9DBA3 | *Lactobacillus kunkeei* |
| A0A0N0CT29 | *Lactobacillus kunkeei* |
| A0A0M9D5K5 | *Lactobacillus kunkeei* |
| A0A0R2DG13 | *Lactobacillus senmaizukei* DSM 21775 |
| A0A0R1R2Q4 | *Lactobacillus spicheri* DSM 15429 |
| A0A0C3AFN0 | *Lactobacillus kunkeei* |
| A0A0P7K1E6 | *Lactobacillus kunkeei* |
| A0A0M9D3N9 | *Lactobacillus apinorum* |
| A0A0R1LK94 | *Lactobacillus acidifarinae* DSM 19394 |
| A0A0H4QX26 | *Lactobacillus koreensis* |
| A0A0R1FXP4 | *Lactobacillus kunkeei* DSM 12361 |
| A0A179CPD2 | *Lactobacillus aviarius* |
| A0A063B938 | *Lactobacillus kunkeei* EFB6 |
| F8I121 | *Weissella koreensis* |
| A0A0R1LJ27 | *Lactobacillus koreensis* JCM 16448 |
| A0A1I4IHB3 | *Lactococcus garvieae* |
| A0A0P7JVB0 | *Lactobacillus kunkeei* |
| A0A1L8CFQ3 | *Lactobacillus kunkeei* |
| A0A0R1FZT1 | *Lactobacillus kunkeei* DSM 12361 |
| A0A179CK20 | *Lactobacillus aviarius* |
| A0A0F3RXX7 | *Lactobacillus spicheri* |
| A0A0R2M4L4 | *Lactobacillus xiangfangensis* |
| A0A0R1MNG9 | *Lactobacillus zymae* DSM 19395 |
| A0A0M9DB36 | *Lactobacillus kunkeei* |
| A0A0R1ZKJ9 | *Lactobacillus aviarius* subsp. *araffinosus* DSM 20653 |
| A0A0P7JT37 | *Lactobacillus kunkeei* |
| A0A0R2LE82 | *Lactobacillus paucivorans* |
| A0A087EP61 | *Lactobacillus kunkeei* |
| A0A0M9DF88 | *Lactobacillus kunkeei* |
| A0A0R2AM78 | *Lactobacillus ozensis* DSM 23829 |
| A0A199QF96 | *Lactobacillus plantarum* |
| A0A0M9DF94 | *Lactobacillus kunkeei* |
| A0A179C4R7 | *Lactobacillus aviarius* |
| A0A0R1R622 | *Lactobacillus paraplantarum* DSM 10667 |
| A0A1Y6JTN4 | *Lactobacillus zymae* |
| A0A0R1YHA3 | *Lactobacillus aviarius* subsp. *aviarius* DSM 20655 |

The hexosaminidases of the invention may be divided into clades or domain groups characterized by their motifs. One aspect of the invention relates to hexosaminidases, e.g., dispersin comprised in the FQS clade. This clade has not been described previously. The clade is termed FQS and polypeptides of this domain comprises Glyco_hydro_20 domain polypeptides of bacterial origin and are in addition to having PNAG activity, characterized by comprising certain motifs. The polypeptides of the clade comprise the motif: [EQ][NRSHA][YVFL][AGSTC][IVLF][EAQYN][SN], corresponding to EHLCFQS at positions 48 to 54 of SEQ ID NO: 3.

One aspect of the invention relates to hexosaminidases, e.g., dispersins comprised in the GADE clade. This clade has not been described previously. The polypeptides of this clade comprise Glyco_hydro_20 domain polypeptides of bacterial origin and are in addition to having PNAG activity, characterized by comprising certain motifs. The polypeptides of the clade comprise the motif example [VLIM][LIV]G[GAV]DE[VI][PSA], corresponding to positions 151 to 158 of SEQ ID NO: 3, where G and DE (corresponding to positions 153 and 155-156 of SEQ ID NO: 3) are fully conserved in GADE clade and part of the active site. Residues D and E are the key catalytic residues of Glyco_hydro_20 enzymes (positions 155 to 156 in SEQ ID NO: 3).

One aspect of the invention relates to hexosaminidases, e.g., dispersins comprised in the GAIL clade. This clade has not been described previously. The polypeptides of this clade comprise Glyco_hydro_20 domain polypeptides of bacterial origin and are in addition to having PNAG activity, characterized by comprising certain motifs. The polypeptides of the clade comprise the motif [GK]A[IL][IL][KSR][LQ]L, corresponding to positions 96 to 102 of SEQ ID NO: 3, where A and L (corresponding to positions 97 and 102 of SEQ ID NO: 3) are fully conserved in GAIL clade and part of the active site.

In one aspect of the invention the hexosaminidase, e.g., dispersins comprises one or more of the following motifs GXDE, [EQ][NRSHA][YVFL][AGSTC][IVLF][EAQYN][SN], [VLIM][LIV]G[GAV]DE[VI][PSA], or [GK]A[IL][IL][KSR][LQ]L. In one aspect, the hexosaminidases comprises the motif GXDE. In one aspect, the hexosaminidases comprises the motif [EQ][NRSHA][YVFL][AGSTC][IVLF][EAQYN][SN]. In one aspect, the hexosaminidases comprises the motif [VLIM][LIV]G[GAV]DE[VI][PSA]. In one aspect, the hexosaminidases comprises the motif [GK]A[IL][IL][KSR][LQ]L.

In one aspect, the hexosaminidase comprises all four motifs GXDE, [EQ][NRSHA][YVFLNAGSTCNIVLFNEAQYNNSN], [VLIM][LIV]G[GAV]DE[VI][PSA], or [GK]A[IL][IL][KSR][LQ]L.

In one aspect, the hexosaminidase comprises the two motifs GXDE and [EQ][NRSHA][YVFLNAGSTCNIVLFNEAQYNNSN].

In one aspect, the hexosaminidase comprises three motifs GXDE, [EQ][NRSHA][YVFL][AGSTC][IVLF][EAQYN][SN] and [VLIM][LIV]G[GAV]DE[VI][PSA]. In one aspect, the hexosaminidase comprises the three motifs GXDE, [EQ][NRSHA][YVFL][AGSTC][IVLF][EAQYN][SN] and [GK]A[IL][IL][KSR][LQ]L.

Figure 2:
FIG. 2. An alignment of the *Lactobacillus* polypeptides of the invention.

An alignment of the polypeptides of the invention is shown in FIG. 2. A phylogenetic tree of the polypeptides of the invention is shown in FIG. 1.

A polypeptide of the present invention preferably has a sequence identity to the mature polypeptide sequence shown in SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 3.

A polypeptide of the present invention preferably has a sequence identity to the mature polypeptide sequence shown in SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 6.

A polypeptide of the present invention preferably has a sequence identity to the mature polypeptide sequence shown in SEQ ID NO: 9 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 9.

A polypeptide of the present invention preferably has a sequence identity to the mature polypeptide sequence shown in SEQ ID NO: 18 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, wherein the polypeptide has hexosaminidase, preferably beta-1,6 N-acetylglucosaminidase activity. In one aspect, the polypeptide differs by up to 10 amino acids, e.g., 1, 2, 3, 4, 5, 6, 7, 8, 9, or 10, from the polypeptide shown in SEQ ID NO: 18.

In an embodiment, the present invention relates to a polypeptide having a sequence identity to the mature polypeptide of SEQ ID NO: 9 of at least 98%, at least 99%, or 100%, wherein the polypeptide has hexosaminidase, preferably beta-1,6 N-acetylglucosaminidase activity. In one aspect, the polypeptides differ by up to 10 amino acids, e.g., 1, 2, 3, 4, 5, 6, 7, 8, 9, or 10, from the mature polypeptide of SEQ ID NO: 9. In an embodiment, the polypeptide has been isolated. A polypeptide of the present invention preferably comprises or consists of the amino acid sequence of SEQ ID NO: 9 or an allelic variant thereof; or is a fragment thereof having hexosaminidase, preferably beta-1,6-N-acetylglucosaminidase activity. In another aspect, the polypeptide comprises or consists of the mature polypeptide of SEQ ID NO: 8. In another aspect, the polypeptide comprises or consists of amino acids 1 to 331 of SEQ ID NO: 8. In another embodiment, the present invention relates to a polypeptide having beta-1,6 N-acetylglucosaminidase activity encoded by a polynucleotide having a sequence identity to the mature polypeptide coding sequence of SEQ ID NO: 7 of at least 98%, at least 99%, or 100%. In a further embodiment, the polypeptide has been isolated.

In an embodiment, the present invention relates to a polypeptide having a sequence identity to the mature polypeptide of SEQ ID NO: 18 of at least 60%, at least 70%, at least 75%, at least 80%, at least 85%, at least 90%, at least 95%, at least 96%, at least 97% at least 98%, at least 99%, at least 98%, at least 99%, or 100%, wherein the polypeptide has hexosaminidase, preferably beta-1,6 N-acetylglucosaminidase activity. In one aspect, the polypeptides differ by up to 10 amino acids, e.g., 1, 2, 3, 4, 5, 6, 7, 8, 9, or 10, from the mature polypeptide of SEQ ID NO: 18. In an embodiment, the polypeptide has been isolated. A polypeptide of the present invention preferably comprises or consists of the amino acid sequence of SEQ ID NO: 18 or an allelic variant thereof; or is a fragment thereof having hexosaminidase, preferably, beta-1,6-N-acetylglucosaminidase activity. In another aspect, the polypeptide comprises or consists of the mature polypeptide of SEQ ID NO: 17. In another aspect, the polypeptide comprises or consists of amino acids 1 to 482 of SEQ ID NO: 17. In another embodiment, the present invention relates to a polypeptide having beta-1,6 N-acetylglucosaminidase activity encoded by a polynucleotide having a sequence identity to the mature polypeptide coding sequence of SEQ ID NO: 16 of at least 60%, at least 70%, at least 75%, at least 80%, at least 85%, at least 90%, at least 95%, at least 96%, at least 97% at least 98%, at least 99%, at least 98%, at least 99%, or 100%. In a further embodiment, the polypeptide has been isolated.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment− Total Number of Gaps in Alignment).

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for hexosaminidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Compositions

The invention relates to the use, methods and detergent compositions comprising *Lactobacillus* hexosaminidases, preferably dispersins.

Liquid Formulations

In one aspect, the cleaning composition is a liquid composition. The hexosaminidase of the invention may be formulated as a liquid enzyme formulation, which is generally a pourable composition, though it may also have a high viscosity. The physical appearance and properties of a liquid enzyme formulation may vary a lot—for example, they may have different viscosities (gel to water-like), be colored, not colored, clear, hazy, and even with solid particles like in slurries and suspensions. The minimum ingredients are the enzyme(s) and a solvent system to make it a liquid.

The solvent system may comprise water, polyols (such as glycerol, (mono, di, or tri) propylene glycol, sugar alcohol (e.g., sorbitol), polypropylene glycol, and/or polyethylene glycol), ethanol, sugars, and salts. Usually, the solvent system also includes a preservation agent and/or other stabilizers.

A liquid enzyme formulation may be prepared by mixing a solvent system and an enzyme concentrate with a desired degree of purity (or enzyme particles to obtain a slurry/suspension).

In an embodiment, the liquid enzyme composition comprises:
(a) at least 0.01% w/w active enzyme protein,
(b) at least 0.5% w/w polyol,
(c) water, and
(d) optionally a preservation agent.

The hexosaminidases, e.g., dispersins in the liquid composition of the invention may be stabilized using conventional stabilizing agents, e.g., a polyol such as propylene glycol or glycerol, ethylene glycol, polyethylene glycol, sugar alcohols, sorbitol, mannitol, erythritol, dulcitol, inositol, xylitol and adonitol.

One embodiment of the invention relates to a composition comprising a *Lactobacillus* hexosaminidase, wherein the composition further comprises:
(a)
i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
ii. optionally one or more enzymes, preferably selected from proteases, amylases or lipases,
iii. optionally one or more surfactants, preferably selected from anionic and nonionic surfactants, or
iv. optionally one or more polymers.

Another preferred embodiment relates to a composition comprising a *Lactobacillus* hexosaminidase, wherein the composition further comprises:
(a)
i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
ii. optionally one or more enzymes, preferably selected from proteases, amylases or lipases,
iii. optionally one or more surfactants, preferably selected from anionic and nonionic surfactants, or
iv. optionally one or more polymers,
wherein the hexosaminidase has N-acetylglucosaminidase activity, preferably β-1,6 N-acetylglucosaminidase activity.

One preferred aspect relates to a composition comprising a dispersin, selected from the group consisting of polypeptides shown in SEQ ID NO: 3, SEQ ID NO: 6, SEQ ID NO: 9, SEQ ID NO: 18 or polypeptides having at least 60%, at least 70%, at least 75%, at least 80%, at least 85%, at least 90%, at least 95%, at least 98% or such as at least 99% sequence identity thereto and wherein the composition further comprises:
i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
ii. optionally one or more enzymes, preferably selected from proteases, amylases or lipases,
iii. optionally one or more surfactants, preferably selected from anionic and nonionic surfactants, or
iv. optionally one or more polymers.

One preferred aspect relates to a composition comprising a polypeptide shown in SEQ ID NO: 3 or a polypeptide having at least 60%, at least 70%, at least 75%, at least 80%, at least 85%, at least 90%, at least 95%, at least 98% or such as at least 99% sequence identity thereto, wherein the composition further comprises:
i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
ii. optionally one or more enzymes, preferably selected from proteases, amylases or lipases,
iii. optionally one or more surfactants, preferably selected from anionic and nonionic surfactants, or
iv. optionally one or more polymers; and wherein the hexosaminidase has N-acetylglucosaminidase activity, preferably β-1,6 N-acetylglucosaminidase activity.

One preferred aspect relates to a composition comprising a polypeptide shown in SEQ ID NO: 6 or a polypeptide having at least 60%, at least 70%, at least 75%, at least 80%, at least 85%, at least 90%, at least 95%, at least 98% or such as at least 99% sequence identity thereto, wherein the composition further comprises:

i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, ii. optionally one or more enzymes, preferably selected from proteases, amylases or lipases, iii. optionally one or more surfactants, preferably selected from anionic and nonionic surfactants, or iv. optionally one or more polymers; and wherein the hexosaminidase has N-acetylglucosaminidase activity, preferably β-1,6 N-acetylglucosaminidase activity.

One preferred aspect relates to a composition comprising a polypeptide shown in SEQ ID NO: 9 or a polypeptide having at least 60%, at least 70%, at least 75%, at least 80%, at least 85%, at least 90%, at least 95%, at least 98% or such as at least 99% sequence identity thereto, wherein the composition further comprises:

i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, ii. optionally one or more enzymes, preferably selected from proteases, amylases or lipases, iii. optionally one or more surfactants, preferably selected from anionic and nonionic surfactants, or iv. optionally one or more polymers; and wherein the hexosaminidase has N-acetylglucosaminidase activity, preferably β-1,6 N-acetylglucosaminidase activity.

One preferred aspect relates to a composition comprising a polypeptide shown in SEQ ID NO: 18 or a polypeptide having at least 60%, at least 70%, at least 75%, at least 80%, at least 85%, at least 90%, at least 95%, at least 98% or such as at least 99% sequence identity thereto, wherein the composition further comprises:

i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, ii. optionally one or more enzymes, preferably selected from proteases, amylases or lipases, iii. optionally one or more surfactants, preferably selected from anionic and nonionic surfactants, or iv. optionally one or more polymers; and wherein the hexosaminidase has N-acetylglucosaminidase activity, preferably β-1,6 N-acetylglucosaminidase activity.

One preferred aspect relates to a composition comprising a *Lactobacillus* hexosaminidase selected from the group shown in Table 1, wherein the composition further comprises:

i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, ii. optionally one or more enzymes, preferably selected from proteases, amylases or lipases, iii. optionally one or more surfactants, preferably selected from anionic and nonionic surfactants, or iv. optionally one or more polymers; and wherein the hexosaminidase has N-acetylglucosaminidase activity, preferably β-1,6 N-acetylglucosaminidase activity.

Granular Formulations

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The hexosaminidase, e.g., *Lactobacillus* hexosaminidase may be formulated as a granule for example as a co-granule that combines one or more enzymes or benefit agents such as MnTACN. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt % zeolite (anhydrous basis); and (c) less than 10 wt % phosphate salt (anhydrous basis), wherein said enzyme co-granule comprises from 10 to 98 wt % moisture sink components and the composition additionally comprises from 20 to 80 wt % detergent moisture sink components. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising a hexosaminidase of the invention. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation. Methods for preparing the core can be found in Handbook of Powder Technology; Particle size enlargement by C. E. Capes; Volume 1; 1980; Elsevier. The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 1% or 5%. The amount may be at most 100%, 70%, 50%, 40% or 30%.

The coating is preferably at least 0.1 μm thick, particularly at least 0.5 μm, at least 1 μm or at least 5 μm. In a one embodiment, the thickness of the coating is below 100 μm. In a more particular embodiment the thickness of the coating is below 60 μm. In an even more particular embodiment the total thickness of the coating is below 40 μm. The coating should encapsulate the core unit by forming a substantially continuous layer. A substantially continuous layer is to be understood as a coating having few or no holes, so that the core unit it is encapsulating/enclosing has few or no uncoated areas. The layer or coating should preferably be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 μm, such as less than 10 μm or less than 5 μm. The salt coating may comprise a single salt or a mixture of two or more salts. The salt may be water soluble, preferably having a solubility of at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. Preferably, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)$_2$HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2 and magnesium acetate.

The salt may be in anhydrous form, or it may be a hydrated salt, i.e., a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H20), zinc sulfate heptahydrate (ZnSO4.7H20), sodium phosphate dibasic heptahydrate (Na2HPO4.7H20), magnesium nitrate hexahydrate (Mg(NO3)$_2$(6H20)), sodium citrate dihydrate and magnesium acetate tetrahydrate. Preferably the salt is applied as a solution of the salt, e.g., using a fluid bed.

In one aspect, the present invention provides a granule, which comprises:
(a) a core comprising a *Lactobacillus* hexosaminidase, e.g dispersin according to the invention, and
(b) optionally a coating consisting of one or more layer(s) surrounding the core.

One aspect of the invention relates to a granule, which comprises:
(a) a core comprising a *Lactobacillus* hexosaminidase, e.g., dispersin, wherein the *Lactobacillus* hexosaminidase is selected from the group consisting of polypeptides shown in SEQ ID NO: 3, SEQ ID NO: 6, SEQ ID NO: 9 or polypeptides having at least 60%, at least 70%, at least 75%, at least 80%, at least 85%, at least 90%, at least 95%, at least 98% or such as at least 99% sequence identity thereto, and
(b) optionally a coating consisting of one or more layer(s) surrounding the core.

One aspect of the invention relates to a granule, which comprises:
(a) a core comprising a polypeptide, selected from the group consisting of polypeptides shown in SEQ ID NO: 3, SEQ ID NO: 6, SEQ ID NO: 9, SEQ ID NO: 18 or polypeptides having at least 60%, at least 70%, at least 75%, at least 80%, at least 85%, at least 90%, at least 95%, at least 98% or such as at least 99% sequence identity thereto, and
(b) optionally a coating consisting of one or more layer(s) surrounding the core.

One aspect of the invention relates to a granule, which comprises:
(a) a core comprising a hexosaminidase selected from the group shown in Table 1, and
(b) optionally a coating consisting of one or more layer(s) surrounding the core.

Another aspect relates to a layered granule comprising
(a) a (non-enzymatic) core;
(b) a coating surrounding the core, wherein the coating comprises *Lactobacillus* hexosaminidase, e.g., dispersin; and
(c) optionally a protective salt coating surrounding the enzyme containing coating.

Another aspect relates to a layered granule comprising
(a) a (non-enzymatic) core;
(b) a coating surrounding the core, wherein the coating comprises *Lactobacillus* hexosaminidase, e.g., dispersin, wherein the *Lactobacillus* hexosaminidase is selected from the group consisting of polypeptides shown in SEQ ID NO: 3, SEQ ID NO: 6, SEQ ID NO: 9 or polypeptides having at least 60%, at least 70%, at least 75%, at least 80%, at least 85%, at least 90%, at least 95%, at least 98% or such as at least 99% sequence identity thereto; and (c) optionally a protective salt coating surrounding the enzyme containing coating.

Another aspect relates to a layered granule comprising
(a) a (non-enzymatic) core;
(b) a coating surrounding the core, wherein the coating comprises a hexosaminidase selected from the group shown in Table 1; and
(c) optionally a protective salt coating surrounding the enzyme containing coating.

Cleaning Compositions

A composition of the invention is preferably a cleaning composition comprising a *Lactobacillus* hexosaminidase in combination with one or more additional cleaning composition components. The choice of additional components is within the skill of the artisan and includes conventional ingredients, including the exemplary non-limiting components set forth below.

One aspect of the invention relates to a composition comprising:
a) at least 0.01 mg/mL of at least one *Lactobacillus* hexosaminidase;
b) at least one cleaning composition component, preferably selected from surfactants, builders, bleach components, polymers, dispersing agents and additional enzymes.

One aspect of the invention relates to a composition comprising:
a) at least 0.01 mg/mL of at least one *Lactobacillus* hexosaminidase, wherein the *Lactobacillus* hexosaminidase is selected from the group shown in Table 1.
b) at least one cleaning composition component, preferably selected from surfactants, builders, bleach components, polymers, dispersing agents and additional enzymes.

One aspect of the invention relates to a composition comprising:
a) at least 0.01 mg/mL of at least one *Lactobacillus* hexosaminidase, wherein the *Lactobacillus* hexosaminidase is selected from polypeptides having at least 60%, at least 70%, at least 75%, at least 80%, at least 85%, at least 90%, at least 95%, at least 96%, at least 97% at least 98%, at least 99%, at least 98%, at least 99%, or 100% sequence identity to the polypeptides shown in SEQ ID NOs: 3, 6 and 9;
b) at least one cleaning composition component, preferably selected from surfactants, builders, bleach components, polymers, dispersing agents and additional enzymes.

One aspect of the invention relates to a composition comprising:
a) at least 0.01 mg/mL of at least one hexosaminidase, wherein the hexosaminidase has at least 60%, at least 70%, at least 75%, at least 80%, at least 85%, at least 90%, at least 95%, at least 96%, at least 97% at least 98%, at least 99%, at least 98%, at least 99%, or 100% sequence identity to the polypeptides shown in SEQ ID NO: 18;

b) at least one cleaning composition component, preferably selected from surfactants, builders, bleach components, polymers, dispersing agents and additional enzymes.

The *Lactobacillus* or *Streptococcus* hexosaminidase may be included in the cleaning, e.g., detergent composition of the present invention at a level of at least 0.0001 to at least 100, at least 0.001 to at least 100, at least 0.01 to at least 100, at least 0.02 to at least 100, at least 0.01 to at least 100, at least 0.1 to at least 100, at least 0.2 to at least 100, at least 0.5 to at least 100 mg/mL, preferably, the concentration of hexosaminidase enzyme in the cleaning composition, e.g., detergent is in the range 0.01 to 100 mg/mL, 0.1 to 50 mg/mL or 0.01 to 10 mg/mL. Thus, the detergent composition may comprise at least 0.00008 wt %, preferably at least 0.002 wt %, 0.003 wt %, 0.004 wt %, 0.005 wt %, 0.006 wt %, 0.008 wt %, 0.01 wt %, 0.02 wt %, 0.03 wt %, 0.05 wt %, 0.1 wt %, 0.2 wt %, 0.3 wt %, 0.4 wt %, 0.6 wt %, 0.7 wt %, 0.8 wt %, 0.9 wt % or 1.0 wt % hexosaminidase, where wt % is the weight percent, which is the mass fraction multiplied by 100. Mass fraction is the ratio of one substance with mass m su b to the mass of the total mixture $m_{fr}(m_{frac}=m_{sub}/m_{tot})$.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to about 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular, from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular, from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01 to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically in the range 40-65%, particularly in the range 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain from about 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly (acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N, N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053.

Bleaching Systems

The cleaning composition may contain 0-50% by weight, such as 1-40%, such as 1-30%, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide—urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyl-diperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic acid (DOBA), sodium 4-(nonanoyloxy)benzene-1-sulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylyl idene)triphenolato-κκ3O]manganese(III). The bleach catalysts may also be other metal compounds; such as iron or cobalt complexes.

In some embodiments, where a source of a peracid is included, an organic bleach catalyst or bleach booster may be used having one of the following formulae:

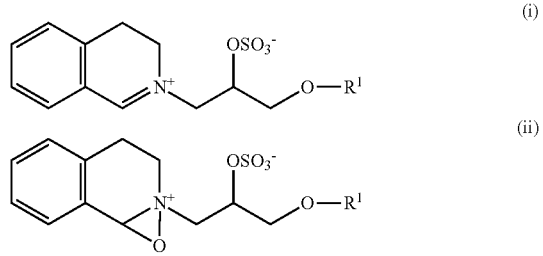

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g., in WO 2007/087258, WO 2007/087244, WO 2007/087259, EP 1867708 (Vitamin K) and WO 2007/087242. Suitable photobleaches may for example be sulfonated zinc or aluminum phthalocyanines.

Metal Care Agents

Metal care agents may prevent or reduce the tarnishing, corrosion or oxidation of metals, including aluminum, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine;

(b) metal salts and complexes chosen from the group consisting of zinc, manganese, titanium, zirconium, hafnium, vanadium, cobalt, gallium and cerium salts and/or complexes, the metals being in one of the oxidation states II, Ill, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The cleaning composition of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt % to about wt %, from about 0.00008 wt % to about 0.05 wt %, or even from about 0.0001 wt % to about wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

Enzymes

The cleaning composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Proteases

Suitable proteases for the compositions of the invention include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO 2009/021867. Subtilisin *lentus*, Subtilisin Novo, subtilisin Carlsberg, *Bacillus licheniformis*, subtilisin BPN', subtilisin 309, subtilisin 147 and subtilisin 168 and, e.g., protease PD138 described in (WO 93/18140). Other useful proteases may be those described in WO 01/16285 and WO 02/016547. Examples of trypsin-like proteases are trypsin (e.g., of porcine or bovine origin) and the *Fusarium* protease described in WO 94/25583 and WO 2005/040372, and the chymotrypsin proteases derived from Cellumonas described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 2007/044993 (Proctor & Gamble/Genencor Int.) such as those derived from *Bacillus amyloliquefaciens*.

Examples of useful proteases are the variants described in: WO 89/06279, WO 92/19729, WO 96/34946, WO 98/20115, WO 98/20116, WO 99/11768, WO 01/44452, WO 2003/006602, WO 2004/03186, WO 2004/041979, WO 2007/006305, WO 2011/036263, WO 2011/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO: 1 of WO 2016/001449. More preferred, the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, 597A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO: 1 of WO 2016/001449, or the *Bacillus amylolichenifaciens* protease (BPN') shown in SEQ ID NO: 2 of WO 2016/001449. The protease variants preferably have at least 80% sequence identity to SEQ ID NO: 1 or SEQ ID NO: 2 of WO 2016/001449.

A protease variant comprising a substitution at one or more positions corresponding to positions 171, 173, 175, 179, or 180 of SEQ ID NO: 1 of WO 2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Enzyme Stabilizers/Inhibitors

The protease, as described above, may be stabilized using conventional stabilizing agents, e.g., a polyol such as glycerol, (mono, di, or tri) propylene glycol, sugar alcohol, polypropylene glycol, and/or polyethylene glycol, preferably polyethylene glycol or polypropylene glycol with a molecular weight in the range of 200-1000; or compounds that act by temporarily reducing the activity of proteases (reversible inhibitors).

Thus, the composition of the invention may also include a protease inhibitor/stabilizer, which is a reversible inhibitor of protease activity, e.g., serine protease activity. Preferably, the protease inhibitor is a (reversible) subtilisin protease inhibitor. In particular, the protease inhibitor may be a peptide aldehyde, boric acid, or a boronic acid; or a derivative of any of these.

The protease inhibitor may have an inhibition constant to a serine protease, Ki (mol/L) of from 1E-12 to 1E-03; more preferred from 1E-11 to 1E-04; even more preferred from 1E-10 to 1E-05; even more preferred from 1E-10 to 1E-06; and most preferred from 1E-09 to 1E-07.

Boronic Acids

The protease inhibitor may be a boronic acid or a derivative thereof; preferably, a phenylboronic acid or a derivative thereof. In an embodiment of the invention, the phenyl boronic acid derivative is of the following formula:

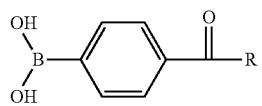

wherein R is selected from the group consisting of hydrogen, hydroxy, C1-C6 alkyl, substituted C1-C6 alkyl, C1-C6 alkenyl and substituted C1-C6 alkenyl. Preferably, R is hydrogen, CH3, CH3CH2 or CH3CH2CH2.

In a preferred embodiment, the protease inhibitor (phenyl boronic acid derivative) is 4-formyl-phenyl boronic acid (4-FPBA).

In another particular embodiment, the protease inhibitor is selected from the group consisting of thiophene-2 boronic acid, thiophene-3 boronic acid, acetamidophenyl boronic acid, benzofuran-2 boronic acid, naphtalene-1 boronic acid, naphtalene-2 boronic acid, 2-FPBA, 3-FBPA, 4-FPBA, 1-thianthrene boronic acid, 4-dibenzofuran boronic acid, 5-methylthiophene-2 boronic, acid, thionaphtrene boronic acid, furan-2 boronic acid, furan-3 boronic acid, 4,4 biphenyl-diborinic acid, 6-hydroxy-2-naphtalene, 4-(methylthio) phenyl boronic acid, 4 (trimethyl-silyl)phenyl boronic acid, 3-bromothiophene boronic acid, 4-methylthiophene boronic acid, 2-naphtyl boronic acid, 5-bromothiphene boronic acid, 5-chlorothiophene boronic acid, dimethylthiophene boronic acid, 2-bromophenyl boronic acid, 3-chlorophenyl boronic acid, 3-methoxy-2-thiophene, p-methyl-phenylethyl boronic acid, 2-thianthrene boronic acid, di-benzothiophene boronic acid, 4-carboxyphenyl boronic acid, 9-anthryl boronic acid, 3,5 dichlorophenyl boronic, acid, diphenyl boronic acidan-hydride, o-chlorophenyl boronic acid, p-chlorophenyl boronic acid, m-bromophenyl boronic acid, p-bromophenyl boronic acid, p-flourophenyl boronic acid, p-tolyl boronic acid, o-tolyl boronic acid, octyl boronic acid, 1,3,5 trimethylphenyl boronic acid, 3-chloro-4-flourophenyl boronic acid, 3-aminophenyl boronic acid, 3,5-bis-(triflouromethyl) phenyl boronic acid, 2,4 dichlorophenyl boronic acid, and 4-methoxyphenyl boronic acid.

Further boronic acid derivatives suitable as protease inhibitors in the detergent composition are described in U.S. Pat. Nos. 4,963,655, 5,159,060, WO 95/12655, WO 95/29223, WO 92/19707, WO 94/04653, WO 94/04654, U.S. Pat. Nos. 5,442,100, 5,488,157 and 5,472,628.

Peptide Aldehyde or Ketone

The protease stabilizer may have the formula: P-(A)y-L-(B)x-B0-R* wherein:

R* is H (hydrogen), $CH_3$, $CX_3$, $CHX_2$, or $CH_2X$, wherein X is a halogen atom, particularly F (fluorine); preferably, R*=H (so that the stabilizer is a peptide aldehyde with the formula P-(A)y-L-(B)x-B0-H);

B0 is a single amino acid residue with L- or D-configuration of the formula —NH—CH(R)—C(=O)—;

(B)x is independently a single amino acid residue, each connected to the next B or to B0 via its C-terminal;

L is absent or independently a linker group of the formula —O(=O)—, —O(=O)—O(=O)—, —C(=S)—, —C(=S)—C(=S)— or —O(=S)—O(=O)—; x is 1, 2 or 3;

A is absent if L is absent or is independently a single amino acid residue connected to L via the N-terminal of the amino acid;

P is selected from the group consisting of hydrogen or if L is absent an N-terminal protection group;

y is 0, 1, or 2,

R is independently selected from the group consisting of $C_{1-6}$ alkyl, $C_{6-10}$ aryl or $C_{7-10}$ arylalkyl, optionally substituted with one or more, identical or different, substituent's R';

R' is independently selected from the group consisting of halogen, —OH, —OR", —SH, —SR", —$NH_2$, —NHR", —NR"$_2$, —$CO_2H$, —$CONH_2$, —CONHR", —CONR"$_2$, —NHC(=N)$NH_2$; and R" is a $C_{1-6}$ alkyl group.

x may be 1, 2 or 3 and therefore B may be 1, 2 or 3 amino acid residues respectively. Thus, B may represent B1, B2-B1 or B3-B2-B1, where B3, B2 and B1 each represent one amino acid residue. y may be 0, 1 or 2 and therefore A may be absent, or 1 or 2 amino acid residues respectively having the formula A1 or A2-A1 wherein A2 and A1 each represent one amino acid residue.

B0 may be a single amino acid residue with L- or D-configuration, which is connected to H via the C-terminal of the amino acid. B0 has the formula —NH—CH(R)—O (=O)—, wherein R is a $C_{1-6}$ alkyl, $C_{6-10}$ aryl or $C_{7-10}$ arylalkyl side chain, such as methyl, ethyl, propyl, isopropyl, butyl, isobutyl, phenyl or benzyl, and wherein R may be optionally substituted with one or more, identical or different, substituents R'. Particular examples of B0 are the D- or L-form of arginine (Arg), 3,4-dihydroxyphenylalanine, isoleucine (Ile), leucine (Leu), methionine (Met), norleucine (Nle), norvaline (Nva), phenylalanine (Phe), m-tyrosine, p-tyrosine (Tyr) and valine (Val). A particular embodiment is when B0 is leucine, methionine, phenylalanine, p-tyrosine and valine.

B1, which is connected to B0 via the C-terminal of the amino acid, may be an aliphatic, hydrophobic and/or neutral amino acid. Examples of B1 are alanine (Ala), cysteine (Cys), glycine (Gly), isoleucine (Ile), leucine (Leu), norleucine (Nle), norvaline (Nva), proline (Pro), serine (Ser), threonine (Thr) and valine (Val). Particular examples of B1 are alanine, glycine, isoleucine, leucine and valine. A particular embodiment is when B1 is alanine, glycine or valine.

If present, B2, which is connected to B1 via the C-terminal of the amino acid, may be an aliphatic, hydrophobic, neutral and/or polar amino acid. Examples of B2 are alanine (Ala), arginine (Arg), capreomycidine (Cpd), cysteine (Cys), glycine (Gly), isoleucine (Ile), leucine (Leu), norleucine (Nle), norvaline (Nva), phenylalanine (Phe), proline (Pro), serine (Ser), threonine (Thr), and valine (Val). Particular examples of B2 are alanine, arginine, capreomycidine, glycine, isoleucine, leucine, phenylalanine and valine. A particular embodiment is when B2 is arginine, glycine, leucine, phenylalanine or valine.

B3, which if present is connected to B2 via the C-terminal of the amino acid, may be a large, aliphatic, aromatic, hydrophobic and/or neutral amino acid. Examples of B3 are isoleucine (Ile), leucine (Leu), norleucine (Nle), norvaline (Nva), phenylalanine (Phe), phenylglycine, tyrosine (Tyr), tryptophan (Trp) and valine (Val). Particular examples of B3 are leucine, phenylalanine, tyrosine and tryptophan.

The linker group L may be absent or selected from the group consisting of —C(=O)—, —C(=O)—C(=O)—, —C(=S)—, —C(=S)—C(=S)— or —C(=S)—C(=O)—. Particular embodiments of the invention are when L is absent or L is a carbonyl group —C(=O)—.

A1, which if present is connected to L via the N-terminal of the amino acid, may be an aliphatic, aromatic, hydrophobic, neutral and/or polar amino acid. Examples of A1 are alanine (Ala), arginine (Arg), capreomycidine (Cpd), glycine (Gly), isoleucine (Ile), leucine (Leu), norleucine (Nle), norvaline (Nva), phenylalanine (Phe), threonine (Thr), tyrosine (Tyr), tryptophan (Trp) and valine (Val). Particular examples of A1 are alanine, arginine, glycine, leucine, phenylalanine, tyrosine, tryptophan and valine. A particular embodiment is when B2 is leucine, phenylalanine, tyrosine or tryptophan.

The A2 residue, which if present is connected to A1 via the N-terminal of the amino acid, may be a large, aliphatic, aromatic, hydrophobic and/or neutral amino acid. Examples of A2 are arginine (Arg), isoleucine (Ile), leucine (Leu), norleucine (Nle), norvaline (Nva), phenylalanine (Phe), phenylglycine, Tyrosine (Tyr), tryptophan (Trp) and valine (Val). Particular examples of A2 are phenylalanine and tyrosine.

The N-terminal protection group P (if present) may be selected from formyl, acetyl (Ac), benzoyl (Bz), trifluoroacetyl, methoxysuccinyl, aromatic and aliphatic urethane protecting groups such as fluorenylmethyloxycarbonyl (Fmoc), methoxycarbonyl (Moc), (fluoromethoxy)carbonyl, benzyloxycarbonyl (Cbz), t-butyloxycarbonyl (Boc) and adamantyloxycarbonyl; p-methoxybenzyl carbonyl, benzyl (Bn), p-methoxybenzyl (PMB), p-methoxyphenyl (PMP), methoxyacetyl, methylamino carbonyl, methylsulfonyl, ethylsulfonyl, benzylsulfonyl, methylphosphoramidyl (MeOP (OH)(=O)) and benzylphosphoramidyl (PhCH$_2$OP(OH) (=O)).

In the case of a tripeptide aldehyde with a protection group (i.e., x=2, L is absent and A is absent), P is preferably acetyl, methoxycarbonyl, benzyloxycarbonyl, methylamino carbonyl, methylsulfonyl, benzylsulfonyl and benzylphosphoramidyl. In the case of a tetrapeptide aldehyde with a protection group (i.e., x=3, L is absent and A is absent), P is preferably acetyl, methoxycarbonyl, methylsulfonyl, ethylsulfonyl and methylphosphoramidyl.

Suitable peptide aldehydes are described in WO 94/04651, WO 95/25791, WO 98/13458, WO 98/13459, WO 98/13460, WO 98/13461, WO 98/13462, WO 2007/141736, WO 2007/145963, WO 2009/118375, WO 2010/055052 and WO 2011/036153. More particularly, the peptide aldehyde may be Cbz-Arg-Ala-Tyr-H, Ac-Gly-Ala-Tyr-H, Cbz-Gly-Ala-Tyr-H, Cbz-Gly-Ala-Tyr-CF$_3$, Cbz-Gly-Ala-Leu-H, Cbz-Val-Ala-Leu-H, Cbz-Val-Ala-Leu-CF$_3$, Moc-Val-Ala-Leu-CF$_3$, Cbz-Gly-Ala-Phe-H, Cbz-Gly-Ala-Phe-CF$_3$, Cbz-Gly-Ala-Val-H, Cbz-Gly-Gly-Tyr-H, Cbz-Gly-Gly-Phe-H, Cbz-Arg-Val-Tyr-H, Cbz-Leu-Val-Tyr-H, Ac-Leu-Gly-Ala-Tyr-H (SEQ ID NO: 19), Ac-Phe-Gly-Ala-Tyr-H (SEQ ID NO: 20), Ac-Tyr-Gly-Ala-Tyr-H (SEQ ID NO: 21), Ac-Phe-Gly-Ala-Leu-H (SEQ ID NO: 22), Ac-Phe-Gly-Ala-Phe-H (SEQ ID NO: 23), Ac-Phe-Gly-Val-Tyr-H (SEQ ID NO: 24), Ac-Phe-Gly-Ala-Met-H (SEQ ID NO: 25), Ac-Trp-Leu-Val-Tyr-H (SEQ ID NO: 26), MeO—CO-Val-Ala-Leu-H, MeNCO-Val-Ala-Leu-H, MeO—CO-Phe-Gly-Ala-Leu-H (SEQ ID NO: 27), MeO—CO-Phe-Gly-Ala-Phe-H (SEQ ID NO: 28), MeSO$_2$-Phe-Gly-Ala-Leu-H (SEQ ID NO: 29), MeSO$_2$-Val-Ala-Leu-H, PhCH$_2$O—P(OH)(O)-Val-Ala-Leu-H, EtSO$_2$-Phe-Gly-Ala-Leu-H (SEQ ID NO: 30), PhCH$_2$SO$_2$-Val-Ala-Leu-H, PhCH$_2$O—P(OH)(O)-Leu-Ala-Leu-H, PhCH$_2$O—P(OH)(O)-Phe-Ala-Leu-H, or MeO—P(OH)(O)-Leu-Gly-Ala-Leu-H (SEQ ID NO: 31). A preferred stabilizer for use in the liquid composition of the invention is Cbz-Gly-Ala-Tyr-H, or a hydrosulfite adduct thereof, wherein Cbz is benzyloxycarbonyl.

Further examples of such peptide aldehydes include a-MAPI, β-MAPI, Phe-C(=O)—Arg-Val-Tyr-H, Phe-C(=O)-Gly-Gly-Tyr-H, Phe-C(=O)-Gly-Ala-Phe-H, Phe-C(=O)-Gly-Ala-Tyr-H, Phe-C(=O)-Gly-Ala-L-H, Phe-C(=O)-Gly-Ala-Nva-H, Phe-C(=O)-Gly-Ala-Nle-H, Tyr-C(=O)—Arg-Val-Tyr-H, Tyr-C(=O)-Gly-Ala-Tyr-H, Phe-C(=S)—Arg-Val-Phe-H, Phe-C(=S)—Arg-Val-Tyr-H, Phe-C(=S)-Gly-Ala-Tyr-H, Antipain, GE20372A, GE20372B, Chymostatin A, Chymostatin B, and Chymostatin C.

The protease stabilizer may be a hydrosulfite adduct of the peptide aldehyde described above, e.g., as described in WO 2013/004636. The adduct may have the formula P-(A)y-L-(B)x-N(H)—CHR—CH(OH)—SO$_3$M, wherein P, A, y, L, B, x and R are defined as above, and M is H or an alkali metal, preferably Na or K.

An aqueous solution of the hydrosulfite adduct may be prepared by reacting the corresponding peptide aldehyde with an aqueous solution of sodium bisulfite (sodium hydrogen sulfite, NaHSO$_3$); potassium bisulfite (KHSO$_3$) by known methods, e.g., as described in WO 98/47523; U.S. Pat. Nos. 6,500,802; 5,436,229; J. Am. Chem. Soc. (1978) 100: 1228; Org. Synth. Coll. 7: 361.

Particularly preferred peptide aldehyde protease stabilizers have the formula P-B3-B2-B1-B0-H, or a hydrosulfite adduct having the formula P-B3-B2-B1-N(H)—CHR—CHOH—SO$_3$M, wherein i) H is hydrogen;
ii) B0 is a single amino acid residue with L- or D-configuration of the formula —NH—CH(R)—C(=O)—;
iii) B1 and B2 are independently single amino acid residues;
iv) B3 is a single amino acid residue, or is absent;
v) R is independently selected from the group consisting of $C_{1-6}$ alkyl, $C_{6-10}$ aryl or $C_{7-10}$ arylalkyl optionally substituted with one or more, identical or different, substituents R';
vi) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;
vii) R" is a $C_{1-6}$ alkyl group;
viii) P is an N-terminal protection group, preferably methoxycarbonyl (Moc) or benzyloxycarbonyl (Cbz); and
ix) M is H or an alkali metal, preferably Na or K.

In an even more preferred embodiment, the peptide aldehyde protease stabilizer has the formula P-B2-B1-B0-H or an adduct having the formula P-B2-B1-N(H)—CHR—CHOH—SO$_3$ M, wherein i) H is hydrogen;
ii) B0 is a single amino acid residue with L- or D-configuration of the formula —NH—CH(R)—C(=O)—;
iii) B1 and B2 are independently single amino acid residues;
iv) R is independently selected from the group consisting of $C_{1-6}$ alkyl, $C_{6-10}$ aryl or $C_{7-10}$ arylalkyl optionally substituted with one or more, identical or different, substituents R';
v) R' is independently selected from the group consisting of halogen, —OH, —OR", —SH, —SR", —NH$_2$, —NHR", —NR"$_2$, —CO$_2$H, —CONH$_2$, —CONHR", —CONR"$_2$, —NHC(=N)NH$_2$;
vi) R" is a $C_{1-6}$ alkyl group;
vii) P is an N-terminal protection group, preferably methoxycarbonyl (Moc) or benzyloxycarbonyl (Cbz); and
viii) M is H or an alkali metal, preferably Na or K.

Preferred embodiments of B0, B1, B2, B3, and P are as described above.

The molar ratio of the above-mentioned peptide aldehydes (or hydrosulfite adducts) to the protease may be at least 1:1 or 1.5:1, and it may be less than 1000:1, more preferred less than 500:1, even more preferred from 100:1 to 2:1 or from 20:1 to 2:1, or most preferred, the molar ratio is from 10:1 to 2:1.

Formate salts (e.g., sodium formate) and formic acid have also shown good effects as inhibitors of protease activity. Formate can be used synergistically with the above-mentioned protease inhibitors, as shown in WO 2013/004635. The formate salts may be present in the slurry composition in an amount of at least 0.1% w/w or 0.5% w/w, e.g., at least 1.0%, at least 1.2% or at least 1.5%. The amount is typically below 5% w/w, below 4% or below 3%.

In an embodiment, the protease is a metalloprotease and the inhibitor is a metalloprotease inhibitor, e.g., a protein hydrolysate based inhibitor (e.g., as described in WO 2008/134343).

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 495257, EP 531372, WO 96/11262, WO 96/29397, WO 98/08940. Other examples are cellulase variants such as those described in WO 94/07998, EP 531315, U.S. Pat. Nos. 5,457,046, 5,686, 593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 02/099091 or a family 44 xyloglucanase, which a xyloglucanase enzyme having a sequence of at least 60% identity to positions 40-559 of SEQ ID NO: 2 of WO 01/62903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly, *B. agaradhaerens, B. licheniformis, B. halodurans, B. clausii*, or *H. insolens*. Suitable mannanases are described in WO 99/64619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas men-*

*docina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase, in particular, the S54V variant used in the commercial product Gentle Power Bleach from Huntsman Textile Effects Pte Ltd (WO 2010/100028).

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID NO: 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO 01/66712 or a variant having at least 90% sequence identity to SEQ ID NO: 12 thereof. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particularly preferred amylases include variants having a deletion of D183 and G184 and having the substitutions R118K, N195F, R320K and R458K, and a variant additionally having substitutions in one or more positions selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™ Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases are comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase.

Haloperoxidases have been isolated from many different fungi, in particular from the fungus group dematiaceous hyphomycetes, such as Caldariomyces, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The cleaning composition of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning composition of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about to about 3% by weight of the composition.

Fluorescent Whitening Agent

The cleaning composition of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning composition of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning composition of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning composition of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g., without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, maltodextrin, polymethacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water-soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Uses

The present invention is also directed to methods for using a hexosaminidase, e.g., a *Lactobacillus* or *Streptococcus* hexosaminidase of the invention and compositions hereof. A hexosaminidase of the invention is useful in cleaning processes typically in laundry/textile/fabric (Household laundry washing, Industrial laundry washing) or hard surface cleaning (ADW, car wash, Industrial surface).

One aspect of the invention relates to the use of a hexosaminidase, e.g., *Lactobacillus* hexosaminidase for cleaning of an item, wherein the item is a textile or a surface. One aspect of the invention relates to the use of a *Lactobacillus* or *Streptococcus* hexosaminidase for cleaning of an item, wherein the item is a textile or a surface, wherein the hexosaminidase is selected from the group consisting of polypeptides shown in SEQ ID NO: 3, SEQ ID NO: 6, SEQ ID NO: 9, SEQ ID NO: 18 and polypeptides having at least 60%, at least 70%, at least 75%, at least 80%, at least 85%, at least 90%, at least 95%, at least 98% or such as at least 99% sequence identity thereto.

One aspect of the invention relates to the use of a *Lactobacillus* hexosaminidase of the invention,
  a) for preventing, reducing or removing stickiness of the item;
  b) for pretreating stains on the item;
  c) for preventing, reducing or removing redeposition of soil during a wash cycle;
  d) for preventing, reducing or removing adherence of soil to the item;
  e) for maintaining or improving whiteness of the item;
  f) for preventing, reducing or removal malodor from the item,
wherein the item is a textile.

One aspect of the invention relates to the use of a *Streptococcus* hexosaminidase of the invention,
  a) for preventing, reducing or removing stickiness of the item;
  b) for pretreating stains on the item;
  c) for preventing, reducing or removing redeposition of soil during a wash cycle;
  d) for preventing, reducing or removing adherence of soil to the item;
  e) for maintaining or improving whiteness of the item;
  f) for preventing, reducing or removal malodor from the item,
wherein the item is a textile.

One aspect of the invention relates to the use of a hexosaminidase, e.g., dispersin, wherein the hexosaminidase is selected from the group consisting of polypeptides shown in SEQ ID NO: 3, SEQ ID NO: 6, SEQ ID NO: 9, SEQ ID NO: 18 and polypeptides having at least 60%, at least 70%, at least 75%, at least 80%, at least 85%, at least 90%, at least 95%, at least 98% or such as at least 99% sequence identity thereto,
  a) for preventing, reducing or removing stickiness of the item;
  b) for pretreating stains on the item;
  c) for preventing, reducing or removing redeposition of soil during a wash cycle;
  d) for preventing, reducing or removing adherence of soil to the item;
  e) for maintaining or improving whiteness of the item;
  f) for preventing, reducing or removal malodor from the item,
wherein the item is a textile.

Use of Cleaning Composition

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein.

One aspect of the invention relates to the use of a composition, preferably a cleaning composition such as a detergent composition comprising a hexosaminidase, e.g., obtained from *Lactobacillus* or *Streptococcus* for cleaning of an item, wherein the item is a textile or a surface.

One aspect of the invention relates to the use of a composition, preferably a cleaning composition such as a detergent composition comprising a hexosaminidase, e.g., obtained from *Lactobacillus* or *Streptococcus* for cleaning of an item, wherein the item is a textile or a surface, wherein the hexosaminidase, e.g., obtained from *Lactobacillus* or *Streptococcus* is selected from the group consisting of polypeptides shown in SEQ ID NO: 3, SEQ ID NO: 6, SEQ ID NO: 9, SEQ ID NO: 18 and polypeptides having at least 60%, at least 70%, at least 75%, at least 80%, at least 85%, at least 90%, at least 95%, at least 98% or such as at least 99% sequence identity thereto.

One aspect of the invention relates to the use of a composition, preferably a cleaning composition such as a detergent composition comprising a hexosaminidase, e.g., obtained from *Lactobacillus* or *Streptococcus* of the invention,
  a) for preventing, reducing or removing stickiness of the item;
  b) for pretreating stains on the item;
  c) for preventing, reducing or removing redeposition of soil during a wash cycle;
  d) for preventing, reducing or removing adherence of soil to the item;
  e) for maintaining or improving whiteness of the item;

f) for preventing, reducing or removal malodor from the item, wherein the item is a textile.

One aspect of the invention relates to the use of a composition, preferably a cleaning composition such as a detergent composition comprising a hexosaminidase, e.g., obtained from *Lactobacillus* or *Streptococcus*, wherein the hexosaminidase is selected from the group consisting of polypeptides shown in SEQ ID NO: 3, SEQ ID NO: 6, SEQ ID NO: 9, SEQ ID NO: 18 and polypeptides having at least 60%, at least 70%, at least 75%, at least 80%, at least 85%, at least 90%, at least 95%, at least 98% or such as at least 99% sequence identity thereto,
   a) for preventing, reducing or removing stickiness of the item;
   b) for pretreating stains on the item;
   c) for preventing, reducing or removing redeposition of soil during a wash cycle;
   d) for preventing, reducing or removing adherence of soil to the item;
   e) for maintaining or improving whiteness of the item;
   f) for preventing, reducing or removal malodor from the item,
wherein the item is a textile.

Methods

The invention further relates to a method of treating a method of treating a fabric comprising:
   (a) contacting the fabric with an aqueous solution of hexosaminidase, e.g., obtained from *Lactobacillus* or *Streptococcus*; and
   (b) optionally rinsing and drying the textile.

One aspect relates to a method of treating a fabric comprising:
   (a) contacting the fabric with an aqueous solution of hexosaminidase, e.g., obtained from *Lactobacillus* or *Streptococcus* is selected from the group consisting of polypeptides shown in SEQ ID NO: 3, SEQ ID NO: 6, SEQ ID NO: 9, SEQ ID NO: 18 and polypeptides having at least 60%, at least 70%, at least 75%, at least 80%, at least 85%, at least 90%, at least 95%, at least 98% or such as at least 99% sequence identity thereto; and
   (b) optionally rinsing and drying the textile.

The invention further relates to a method for cleaning or laundering an item comprising the steps of:
   a. exposing an item to a wash liquor comprising a hexosaminidase, e.g., obtained from *Lactobacillus* or *Streptococcus* of the invention or a detergent composition comprising a hexosaminidase;
   b. completing at least one wash cycle; and
   c. optionally rinsing the item,
wherein the item is a fabric.

The invention further relates to a method for cleaning or laundering an item comprising the steps of:
   a. exposing an item to a wash liquor comprising a hexosaminidase, e.g., obtained from *Lactobacillus* or *Streptococcus* of the invention or a detergent composition comprising a hexosaminidase, wherein the hexosaminidase is selected from the group consisting of polypeptides shown in SEQ ID NO: 3, SEQ ID NO: 6, SEQ ID NO: 9, SEQ ID NO: 18 and polypeptides having at least 60%, at least 70%, at least 75%, at least 80%, at least 85%, at least 90%, at least 95%, at least 98% or such as at least 99% sequence identity thereto;
   b. completing at least one wash cycle; and
   c. optionally rinsing the item, wherein the item is a fabric.

One embodiment relates to a method, wherein the *Lactobacillus* hexosaminidase comprises one or more of the following motifs GXDE, [EQ][NRSHA][YVFLNAGSTC-NIVLFNEAQYNNSN], [VLIM][LIV]G[GAV]DE[VI][PSA], or [GK]A[IL][IL][KSR][LQ]L.

One embodiment relates to a method, wherein the *Lactobacillus* hexosaminidase comprises the motifs GXDE and [EQ][NRSHA][YVFL][AGSTC][IVLF][EAQYN][SN].

One embodiment relates to a method, wherein the *Lactobacillus* hexosaminidase comprises the motifs [VLIM][LIV]G[GAV]DE[VI][PSA] and/or [GK]A[IL][IL][KSR][LQ]L.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of to 80° C., in the range of 10° C. to 70° C., in the range of 10° C. to 60° C., in the range of 10° C. to in the range of 15° C. to 40° C. or in the range of 20° C. to 30° C. In one aspect, the temperature of the wash liquor is 30° C.

The concentration of the hexosaminidase in the wash liquor is typically in the range of at least 0.00001 ppm to at least 10 ppm, at least 0.00002 ppm to at least 10 ppm, at least 0.0001 ppm to at least 10 ppm, at least 0.0002 ppm to at least 10 ppm, at least 0.001 ppm to at least 10 ppm, at least 0.002 ppm to at least 10 ppm, at least 0.01 ppm to at least 10 ppm, at least 0.02 ppm to at least 10 ppm, at least 0.1 ppm to at least 10 ppm, at least 0.2 ppm to at least 10 ppm, at least 0.5 ppm to at least 5 ppm.

Definitions

Biofilm is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp. In one aspect, the biofilm producing strain is *Brevundimonas* sp. In one aspect, the biofilm producing strain is *Pseudomonas*, e.g., *Pseudomonas alcaliphila* or *Pseudomonas fluorescens*. In one aspect, the biofilm producing strain is *Staphylococcus aureus*.

The term "deep cleaning" means disruption or removal of components of organic matter, e.g., biofilm, such as polysaccharides, e.g., PNAG, proteins, DNA, soil or other components present in the organic matter.

Cleaning component: The cleaning component is different to the hexosaminidase. The precise nature of these additional components (e.g., adjuncts), and levels of incorporation thereof, will depend on the physical form of the composition and the nature of the operation for which it is to be used. Suitable cleaning component materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, antifoaming agents, dispersants, processing aids, and/or pigments.

Cleaning Composition: The term "cleaning or detergent composition" refers to compositions that find use in the removal of undesired compounds from items to be cleaned, such as textiles. The cleaning composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxidoreductases, bluing agents and fluorescent dyes, antioxidants, and solubilizers.

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains or soil present on the object to be cleaned during, e.g., wash or hard surface cleaning.

The term "whiteness" is defined herein as the quality or state of a textile of being white. Loss of whiteness may be due to removal of optical brighteners/hueing agents and result in a greying or yellowing of the textiles. Greying and yellowing can be due to soil redeposition, body soils, colouring from, e.g., iron and copper ions or dye transfer. Whiteness might include one or several issues from the list below: colourant or dye effects; incomplete stain removal (e.g., body soils, sebum etc.); redeposition (greying, yellowing or other discolourations of the object) (removed soils reassociate with other parts of textile, soiled or unsoiled); chemical changes in textile during application; and clarification or brightening of colours.

The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

The term "malodor" means an odor which is not desired on clean items. The cleaned item should smell fresh and clean without malodors adhered to the item. One example of malodor is compounds with an unpleasant smell, which may be produced by microorganisms. Another example of unpleasant smell can be sweat or body odor adhered to an item which has been in contact with human or animal. Another example of malodor can be the odor from spices, which sticks to items for example curry or other exotic spices which smell strongly, tobacco, cooking smell (fried oil, fish etc.), scents of perfume such as deodorant and eau de cologne.

The term "mature polypeptide" means a polypeptide in its final form following translation and any post-translational modifications, such as N-terminus processing, C-terminus truncation, glycosylation, phosphorylation, etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g., originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g., polyamide fiber, acrylic fiber, polyester fiber, polyvinyl chloride fiber, polyurethane fiber, polyurea fiber, aramid fiber), and/or cellulose-containing fiber (e.g., rayon/viscose, ramie, flax/linen, jute, cellulose acetate fiber, lyocell). Fabric may be conventional washable laundry, for example, stained household laundry. When the term fabric or garment is used, it is intended to include the broader term textiles as well.

The term "variant" means a polypeptide having the activity of the parent or precursor polypeptide and comprising an alteration, i.e., a substitution, insertion, and/or deletion, at one or more (e.g., several) positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues x 100)/(Length of Alignment—Total Number of Gaps in Alignment).

Clade: a group of polypeptides clustered together based on homologous features traced to a common ancestor. Polypeptide clades can be visualized as phylogenetic trees and a clade is a group of polypeptides that consists of a common ancestor and all its lineal descendants.

Nomenclature

For purposes of the present invention, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 natural amino acids.

Unless otherwise indicated, or if it is apparent from the context that something else is intended, all percentages are percentage by weight (% w/w) or (wt %).

The invention is further described in the following non-limiting paragraphs:

1. A cleaning composition comprising at least 0.01 mg *Lactobacillus* hexosaminidase and a cleaning component, wherein the cleaning component is
   (a) at least one surfactant;
   (b) at least one builder; or
   (c) at least one polymer.

2. The composition of paragraph 1, wherein the composition comprises from about 1% to about 40% by weight of an anionic surfactant, such as from about 5% to about 30%, including from about 5% to about 15%, or from about 15% to about 20%, or from about 20% to about 25% anionic surfactant, preferably selected from linear alkylbenzenesulfonates (LAS), isomers of LAS, branched alkyl benzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

3. The composition of paragraph 1 or 2, comprising from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12% of at least one nonionic surfactant, preferably selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.

4. The composition of any of paragraphs 1 to 3, wherein the composition comprises from about 1 wt % to about 60 wt %, from about 5 wt % to about 50 wt %, from about 10 wt % to about wt % of at least one builder, preferably selected from citric acid, methylglycine-N,N-diacetic acid (MGDA) and/or glutamic acid-N,N-diacetic acid (GLDA) and mixtures thereof.

5. The composition of any of paragraphs 1 to 4, wherein the composition 0-50% by weight, such as 1-40%, such as 1-30%, such as about 1% to about 20% of at least one bleach component preferably selected from a peroxide, preferably, percabonate and a catalyst preferably a metal-containing bleach catalyst such as 1,4,7-trimethyl-1,4,7-triazacyclononane or manganese (II) acetate tetrahydrate (MnTACN).

6. The composition of any of paragraphs 1 to 5, wherein the *Lactobacillus* hexosaminidase comprises the one or more of the motifs GXDE, [EQ][NRSHA][YVFLNAGSTCNIVLFNEAQYNNSN], [VLIM][LIV]G[GAV]DE[VI][PSA], or [GK]A[IL][IL][KSR][LQ]L.

7. The composition of any of paragraphs 1 to 6, wherein the *Lactobacillus* hexosaminidase comprises the motifs GXDE and [EQ][NRSHA][YVFL][AGSTC][IVLF][EAQYN][SN].

8. The composition of paragraph 7, wherein the *Lactobacillus* hexosaminidase comprises the motifs [VLIM][LIV]G[GAV]DE[VI][PSA] and/or [GK]A[IL][IL][KSR][LQ]L.

9. The composition of any of paragraphs 1 to 8, wherein the *Lactobacillus* hexosaminidase is selected from the group consisting of polypeptides having the amino acid sequence of SEQ ID NO: 3, SEQ ID NO: 6, SEQ ID NO: 9, and polypeptides having at least 60%, at least 70%, at least 75%, at least 80%, at least 85%, at least 90%, at least 95%, at least 98% or such as at least 99% sequence identity thereto.

10. The composition of any of paragraphs 1 to 9, wherein the polypeptide having hexosaminidase activity comprises the amino acid sequence of SEQ ID NO: 3 or polypeptides having at least 60%, e.g., 80%, 85%, 90%, 95%, 98% or 99% sequence identity thereto.

11. The composition of any of paragraphs 1 to 10, wherein the polypeptide having hexosaminidase activity comprises the amino acid sequence of SEQ ID NO: 6 or polypeptides having at least 60%, e.g., 80%, 85%, 90%, 95%, 98% or 99% sequence identity thereto.

12. The composition of any of paragraphs 1 to 11, wherein the polypeptide having hexosaminidase activity comprises the amino acid sequence of SEQ ID NO: 9 or polypeptides having at least 60%, e.g., 80%, 85%, 90%, 95%, 98% or 99% sequence identity thereto.

13. The composition of any of paragraphs 1 to 12, wherein the composition further comprises one or more enzymes selected from the group consisting of proteases, lipases, cutinases, amylases, carbohydrases, cellulases, pectinases, mannanases, arabinases, galactanases, xylanases and oxidases.

14. Use of a composition of any of paragraphs 1 to 13 for cleaning of an item, wherein the item is a textile or a surface.

15. Use of a composition of paragraph 14, preferably a cleaning composition such as a detergent composition comprising a *Lactobacillus* hexosaminidase,
   a) for preventing, reducing or removing stickiness of the item;
   b) for pretreating stains on the item;
   c) for preventing, reducing or removing redeposition of soil during a wash cycle;
   d) for preventing, reducing or removing adherence of soil to the item;
   e) for maintaining or improving whiteness of the item;
   f) for preventing, reducing or removing malodor from the item,
wherein the item is a textile.

16. Use of paragraph 14 or 15, wherein the *Lactobacillus* hexosaminidase comprises one or more of the following motifs GXDE, [EQ][NRSHA][YVFL][AGSTC][IVLF][EAQYN][SN], [VLIM][LIV]G[GAV]DE[VI][PSA], or [GL]A[IL][IL][KSR][LQ]L.

17. Use of any of paragraphs 14 to 16, wherein the *Lactobacillus* hexosaminidase comprises the motifs GXDE and [EQ][NRSHA][YVFL][AGSTC][IVLF][EAQYN][SN].

18. Use of any of paragraphs 14 to 16, wherein the *Lactobacillus* hexosaminidase comprises the motifs [VLIM][LIV]G[GAV]DE[VI][PSA] and/or [GK]A[IL][IL][KSR][LQ]L.

19. Use of any of paragraphs 14 to 18, wherein the *Lactobacillus* hexosaminidase is selected from the group consisting of polypeptides shown in SEQ ID NO: 3, SEQ ID NO: 6, SEQ ID NO: 9, or polypeptides having at least 60%, at least 70%, at least 75%, at least 80%, at least 85%, at least 90%, at least 95%, at least 98% or such as at least 99% sequence identity thereto.

20. A method of formulating a cleaning composition, comprising adding a *Lactobacillus* hexosaminidase and at least one cleaning component.

21. A kit intended for cleaning, wherein the kit comprises a solution of an enzyme mixture comprising *Lactobacillus* hexosaminidase, and an additional enzyme selected from proteases, amylases, cellulases and lipases.

22. A method of treating a fabric comprising:
   (a) contacting the fabric with an aqueous solution of *Lactobacillus* hexosaminidase;
   (b) and optionally rinsing and drying the textile.

23. A method for cleaning or laundering an item comprising the steps of:
   (a) exposing an item to a wash liquor comprising a *Lactobacillus* hexosaminidase of the invention or a detergent composition comprising a *Lactobacillus* hexosaminidase;
   (b) completing at least one wash cycle; and
   (c) optionally rinsing the item, wherein the item is a fabric.

24. The method of paragraph 22 or 23, wherein the *Lactobacillus* hexosaminidase comprises one or more of the following motifs GXDE, [EQ][NRSHA][YVFL][AGSTC][IVLF][EAQYN][SN], [VLIM][LIV]G[GAV]DE[VI][PSA], or [GL]A[IL][IL][IL][KSR][LQ]L.

25. The method of any of paragraphs 22 to 24, wherein the *Lactobacillus* hexosaminidase comprises the motifs GXDE and [EQ][NRSHA][YVFL][AGSTC][IVLF][EAQYN][SN].

26. The method of paragraph 25, wherein the *Lactobacillus* hexosaminidase comprises the motifs [VLIM][LIV]G[GAV]DE[VI][PSA] and/or [GL]A[IL][IL][IL][KSR][LQ]L.

27. The method of any of paragraphs 22 to 26, wherein the *Lactobacillus* hexosaminidase is selected from the group consisting of polypeptides shown in SEQ ID NO: 3, SEQ ID NO: 6, SEQ ID NO: 9, or polypeptides having at least 60%, at least 70%, at least 75%, at least 80%, at least 85%, at least 90%, at least 95%, at least 98% or such as at least 99% sequence identity thereto.

EXAMPLES

Assays
Wash Assay
Mini Launder-O-Meter (MiniLOM) Model Wash System
   MiniLOM is a mini wash system in which washes are performed in 50 ml test tubes placed in a Stuart rotator. Each tube simulates one small washing machine and during an experiment, each will contain a solution of a specific detergent/enzyme system to be tested along with the soiled and unsoiled fabrics it is tested on. Mechanical stress is achieved via rotation (typically 20 rpm), and the temperature is controlled by placement of the rotator in a heating cabinet/room.
Assay I: Testing of Hexosaminidase Activity
   The hexosaminidase activity of the polypeptides listed in the table below was determined using 4-Methylumbelliferyl N-acetyl-p-D-glucosaminide (Sigma-Aldrich) as substrate. The enzymatic reaction was performed in triplicates in a 96 well flat bottom polystyrene microtiter plate (Thermo Scientific) with the following conditions: 20 mM 3-(N-morpholino) propanesulfonic acid pH7 buffer, 5 mM 4-Methylumbelliferyl N-acetyl-p-D-glucosaminide, 0.01 vol % (% w/w) Brij (Polyoxyethylene lauryl ether, CAS 9002-92-0) and 50 nM purified enzyme sample in a total reaction volume of 200 µl. Blank samples without polypeptide were run in parallel. The reactions were carried out at room temperature using a SpectraMax M2e Microplate Reader from Molecular Devices. Excitation wavelength was set to 368 nm and emission wavelength to 448 nm. Fluorescent signal was followed for 15 min in Kinetic Mode. Initial rate of reaction was evaluated in units of RFU/min by calculating the maximum initial increase in fluorescent signal over time as 4-Methylumbelliferyl was released from 4-Methylumbelliferyl N-acetyl-p-D-glucosaminide substrate due to enzymatic reaction.
Composition of Model Detergent A (Liquid)
   Ingredients: 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w).
Composition of Model Detergent T (Powder)
   Ingredients: 11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).
   Triple-20 Nonionic Model Detergent was prepared by dissolving 3.33 g/l non-ionic detergent containing NaOH 0.87%, MPG (Monopropylenglycol) 6%, Glycerol 2%, Soap-soy 2.75%, Soap-coco 2.75%, PCA (Sokalon CP-5) 0.2%, AEO Biosoft N25-7(NI) 16%, Sodium formate 1%, Sodium Citrate 2%, DTMPA 0.2%, Ethanol (96%) 3%, adjustment of pH with NaOH or Citric acid ass water to 100% (all percentages are w/w (weight volume) in water with hardness 15 dH.

Composition of Persil Universal Gel

Ingredients: 15-30% anionic surfactants, 5-15% nonionic surfactant, <5% Phosphonate, soap, perfume, optical brightener and enzymes.

Example 1: Strain and DNA

The gene sequence encoding the hexosaminidase polypeptides from the strains *Lactobacillus paraplantarum* DSM 10667 and *Lactobacillus apinorum* respectively were found in the public database (Accession number SWISSPROT: A0A0R1R622 and EMBLWGS:AZE001000001 for SEQ ID NO: 1 and SWISSPROT:AOAOM9D3N9 and EMBLWGS: JXCT01000010 for SEQ ID NO: 4).

The DNA encoding the hexosaminidase having the polypeptide comprised in SEQ ID NO: 8 was isolated from a *Lactobacillus paraplantarum* bacterial strain, isolated from an environmental sample collected in Germany. Chromosomal DNA from the *Lactobacillus paraplantarum* strain was isolated by QIAamp DNA Blood Mini Kit (Qiagen, Hilden, Germany) and subjected to full genome sequencing using Illumina technology. The genome sequence was analyzed for protein sequences that have glycosyl hydrolase domains (GH20, www.cazy.org). One gene with corresponding sequence SEQ ID NO: 7 was subsequently identified.

The codon optimized synthetic DNA encoding the mature peptide sequences of two hexosaminidases with SEQ ID NOs: 3 and 6 were ordered from the company Geneart.

TABLE 2

| SEQ ID | Donor | country of origin |
|---|---|---|
| SEQ ID NO: 3 | *Lactobacillus paraplantarum* DSM 10667 | France |
| SEQ ID NO: 6 | *Lactobacillus apinorum* | Sweden |
| SEQ ID NO. 9 | *Lactobacillus paraplantarum* | Germany |
| SEQ ID NO: 18* | *Streptococcus merionis* | Germany |

*The dispersin comprising the amino acids sequence shown in SEQ ID NO: 18 was expressed and purified as described in example 1 or 2 for the *Lactobacillus*.

Example 2: Cloning and Expression of Glycol_Hydro_20 Hexosaminidases

The codon optimized synthetic genes encoding the mature peptide sequences of the hexosaminidases with SEQ ID NOs: 3 and 6 were inserted into a *Bacillus* expression vector as described in WO 2012/025577. Briefly, the DNA encoding the mature peptide of the glycol_hydro_20 hexosaminidase gene was cloned in frame to a *Bacillus clausii* secretion signal (BcSP; with the following amino acid sequence: MKKPLGKIVASTALLISVAFSSSIASA (SEQ ID NO: 10). BcSP replaced the native secretion signal in the gene. Downstream of the BcSP sequence, an affinity tag sequence was introduced to ease the purification process (His-tag; with the following amino acid sequence: HHHHHHPR (SEQ ID NO: 11). The gene that was expressed therefore comprised the BcSP sequence followed by the His-tag sequence followed by the mature wild type glycol_hydro_20 sequence. The DNA encoding the mature peptide of the glycol_hydro_20 beta-hexosaminidase gene SEQ ID NO: 9 was amplified from the *Lactobacillus paraplantarum* genomic DNA by standard PCR techniques using specific primers containing an overhang to the cloning vector. The gene was consecutively cloned in frame to a *Bacillus clausii* secretion signal as described above. The final expression plasmid (BcSP-His-tag-glycol_hydro_20) was transformed into a *Bacillus subtilis* expression host. The glycol_hydro_20 BcSP-fusion gene was integrated by homologous recombination into the *Bacillus subtilis* host cell genome upon transformation. The gene construct was expressed under the control of a triple promoter system (as described in WO 99/43835). The gene coding for chloramphenicol acetyltransferase was used as maker (as described in (Diderichsen et al., 1993, *Plasmid* 30: 312-315)). Transformants were selected on LB media agar supplemented with 6 micrograms of chloramphenicol per ml. One recombinant *Bacillus subtilis* clone containing the glycol_hydro_20 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

Example 3: His Tag Purification Method

The His-tagged glycol_hydro_20 hexosaminidase enzymes were purified by immobilized metal chromatography (IMAC) using $Ni^{2+}$ as the metal ion on 5 mL HisTrap Excel columns (GE Healthcare Life Sciences). The purification took place at pH7 and the bound protein was eluted with imidazole. The purity of the purified enzymes was checked by SDS-PAGE and the concentration of the enzyme determined by Absorbance 280 nm after a buffer exchange in 50 mM HEPES, 100 mM NaCl pH7.0

```
SEQ ID NO: 10:
MKKPLGKIVASTALLISVAFSSSIASA

SEQ ID NO: 11:
HHHHHHPR
```

Example 4: Biofilm Growth and Detachment Assay

*Staphylococcus aureus* 15981 was kindly provided by Iñigo Lasa (Valle et al., 2003, *Mol Microbiol.* 48(4):1075-87). The strain was grown on trypticase soy agar (TSA) at 37° C. overnight. Next day, a single colony was transferred to 15 ml tripticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L non-ionic detergent or 3.3 gr/L model A detergent (composition hard water and non-ionic and model A) containing 0 (control) or 20, 10, 5, 2.5, 1.25, 0.62, 0.31, 0.16, 0.08, 0.04, 0.02 and 0.01 µg/mL of enzyme SEQ ID NOs: 3, 6 and 9. After incubation at 37° C. for 1 hour, wells were washed with water and stained for 15 min with 100 µL of 0.095% crystal violet solution (SIGMA V5265). Wells were then rinsed twice with 100 µL water, dried and the plates were scanned.

The lowest concentration of each enzyme that could remove the visible formation of biofilm of *S. aureus* 15981 after 1 hour incubation, in the presence and absence of detergent was determined (see Table 3). All enzymes were assayed per duplicate in three independent assays. The average of the minimal concentration of enzyme that removed the visible formation of *S. aureus* 15981 from the three assays is listed in Table 3.

Table 3. Minimal concentration of enzyme that can remove the visible formation of *S. aureus* 15981 after 1 hour incubation in either hard water or model A detergent

TABLE 3

| SEQ ID | Minimal concentration for biofilm removal in hard water μg/mL | Minimal concentration for biofilm removal in non-ionic detergent μg/mL | Minimal concentration for biofilm removal in model A detergent μg/mL |
|---|---|---|---|
| 3 | 0.04 | 0.16 | 0.16 |
| 6 | 0.62 | 2.08 | 3.75 |
| 9 | 13.33 | 13.33 | >20 |

Example 5: Cleaning Properties of Powder Model Detergents

A crude EPS (extracellular polymeric substances) extract was prepared from *Pseudomonas fluorescens* (Isolate from Iceland) as follows: *P. fluorescens* was restreaked on TSA and incubated for 1 day at 20° C. The strain was inoculated in TSB and incubated 0/N at After propagation, the culture was diluted (1:100) in M63 supplemented medium (15 mM $(NH_4)_2SO_4$, 100 mM $KH_2PO_4$, 1.8 μM $FeSO_4$, 1 mM $MgSO_4 \cdot 7H2O$, 0.4% (w/v) glycerol, 0.2% (w/v) Casamino acids and 0.0001% (w/v) Thiamine), added to a Corning® CellBIND® 225 cm 2 Angled Neck Cell Culture Flasks with Vent Cap (400 ml per flask) and incubated statically for 3 days at 20° C. The biofilm culture was subsequently pelleted by centrifugation (10 min, 8000 g, 25° C.), and the cells were resuspended in 3 M NaCl (4 ml per flask) and incubated for 30 min at 30° C. to extract the surface-associated EPS. The EPS-containing supernatant obtained after centrifugation (10 min, 5000 g, 25° C.) was stored at −20° C. until further use.

For wash performance testing, 50 ul aliquots of the crude EPS extract was spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 5.3 g/L model T powder detergent) and enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and left to dry on filter paper overnight. The remission ($REM^{460nm}$) values were measured using a Macbeth Color-Eye 7000 (CE7000), and are displayed in table 4. Delta values ($REM^{460nm}_{(washed\ with\ enzyme)} - REM^{460nm}_{(washed\ without\ enzyme)}$) are also indicated.

Example 6. Cleaning Properties of Hexosaminidases in Liquid Model Detergents

A crude extract of biofilm extracellular polymeric substances (EPS) was prepared from *Staphylococcus aureus* 15981 (kind gift from Iñigo Lasa (Valle et al., 2003, *Mol. Microbiol.* 48:1075-1087) as follows: 500 mL of TSB+1% glucose (24563; Roquette Freres) was inoculated, aliquoted into 50 ml conical centrifuge tubes (339652; Thermo Scientific Nunc) and incubated for 24 hours at 37° C. under shaking conditions (200 rpm). Following incubation, the cells were pelleted by centrifugation (10 min, 6000 g, 25° C.), pooled and resuspended in 4 ml 3 M NaCl. The suspension was vortexed vigorously and incubated for 15 min at ambient temperature to extract the surface-associated EPS. The cells were then re-pelleted (10 min, 5000 g, 25° C.) and the EPS-containing supernatant was retrieved. Milli-Q water was added (6 ml) and the solution was sterile-filtered twice (0.45 μm followed by 0.2 μm). The crude extract was stored at −20° C. until further use. For wash performance testing, 50 ul aliquots of the crude EPS extract was spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 3.33 g/L liquid model A detergent or 3.33 g/L nonionic model detergent) and enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and left to dry on filter paper overnight. The remisssion ($REM^{460nm}$) values were measured using a Macbeth Color-Eye 7000 (CE7000), and are displayed in tables 5 and 6. Delta values ($REM^{460nm}_{(washed\ with\ enzyme)} - REM^{460nm}_{(washed\ without\ enzyme)}$) are also indicated.

TABLE 4

Cleaning effects of hexosaminidase (SEQ ID NO: 3) in powder model detergent T

| Swatch | Enzyme | Enzyme concentration (μg/ml) | Average REM(460 nm) | ΔREM(460 nm) |
|---|---|---|---|---|
| wfk20A | No enzyme | 0 | 61.4 | |
| wfk20, EPS | No enzyme | 0 | 52.8 | |
| wfk20, EPS | SEQ ID NO: 3 | 0.2 | 60.5 | 7.6 |
| wfk20, EPS | SEQ ID NO: 3 | 2 | 67.5 | 14.6 |

TABLE 5

Cleaning effects in liquid model detergent A

| Swatch | Enzyme | Enzyme concentration (µg/ml) | REM(460 nm) | ΔREM |
|---|---|---|---|---|
| wfk20A | No enzyme | 0.0 | 58.5 | |
| EPS | No enzyme | 0.0 | 30.1 | |
| EPS | SEQ ID NO: 3 | 2.0 | 65.5 | 35.4 |
| EPS | SEQ ID NO: 3 | 0.2 | 58.2 | 28.1 |
| EPS | SEQ ID NO: 9 | 2.0 | 38.6 | 8.5 |
| EPS | SEQ ID NO: 9 | 0.2 | 32.1 | 2.0 |

TABLE 6 cleaning effects in liquid nonionic model detergent

| Swatch | Enzyme | Enzyme concentration (µg/ml) | REM(460 nm) | ΔREM |
|---|---|---|---|---|
| wfk20A | No enzyme | 0.0 | 59.7 | |
| EPS | No enzyme | 0.0 | 30.4 | |
| EPS | SEQ ID NO: 3 | 20.0 | 63.2 | 32.8 |
| EPS | SEQ ID NO: 3 | 2.0 | 61.3 | 30.8 |
| EPS | SEQ ID NO: 3 | 0.2 | 60.9 | 30.4 |
| EPS | SEQ ID NO: 6 | 20.0 | 46.1 | 15.6 |
| EPS | SEQ ID NO: 6 | 2.0 | 33.6 | 3.1 |
| EPS | SEQ ID NO: 6 | 0.2 | 31.3 | 0.9 |
| EPS | SEQ ID NO: 9 | 20.0 | 63.9 | 33.4 |
| EPS | SEQ ID NO: 9 | 2.0 | 45.4 | 15.0 |
| EPS | SEQ ID NO: 9 | 0.2 | 34.4 | 4.0 |

Example 7: Construction of Clades and Phylogenetic Trees

The Glyco_hydro_20 domain includes the polypeptides of the invention having hexosaminidase, e.g., PNAG activity and comprises the FQS, GADE and/or GAIL clades.

A phylogenetic tree was constructed, of polypeptide sequences containing a Glyco_hydro_20 domain, as defined in PFAM (PF00728, Pfam version 31.0 Finn, 2016, Nucleic Acids Research, Database Issue 44: D279-D285). The phylogenetic tree was constructed from a multiple alignment of mature polypeptide sequences containing at least one Glyco_hydro_20 domain. The sequences were aligned using the MUSCLE algorithm version 3.8.31 (Edgar, 2004, Nucleic Acids Research 32(5): 1792-1797), and the trees were constructed using FastTree version 2.1.8 (Price et al., 2010, PloS one 5(3)) and visualized using iTOL (Letunic & Bork, 2007 Bioinformatics 23(1): 127-128). The polypeptide sequences containing a Glyco_hydro_20 domain comprises several motifs; one example is GXDE, situated in positions 153 to 156 in Lactobacillus paraplantarum (SEQ ID NO: 3). Residues D and E are the key catalytic residues of Glyco_hydro_20 enzymes (positions 155 to 156 in SEQ ID NO: 3).

The polypeptides in Glyco_hydro_20 can be separated into multiple distinct sub-clusters, or clades as listed below. The distinct motifs for each clade are described in detail below.

Generation of FQS clade

A clade, preferably shared by the polypeptides of the invention, was identified. This clade has not been described previously. The clade is termed FQS and polypeptides of this clade comprises Glyco_hydro_20 domain polypeptides of bacterial origin and are in addition to having PNAG activity, characterized by comprising a certain motif. The polypeptides of the clade comprise the motif example [EQ][NR-SHA][YVFL][AGSTC][IVLF][EAQYN][SN], corresponding to EHLCFQS at positions 48 to 54 of SEQ ID NO: 3.

Generation of GADE clade

A clade, preferably shared by the polypeptides of the invention, was identified. This clade has not been described previously. The clade is termed GADE and polypeptides of this clade comprise Glyco_hydro_20 domain polypeptides of bacterial origin and are in addition to having PNAG activity, characterized by comprising certain motifs. The polypeptides of the clade comprise the motif example [VLIM][LIV]G[GAV]DE[VI][PSA], corresponding to positions 151 to 158 of SEQ ID NO: 3, where G and DE (corresponding to positions 153 and 155-156 of SEQ ID NO: 3) are fully conserved in GADE clade and part of the active site. Residues D and E are the key catalytic residues of Glyco_hydro_20 enzymes (positions 155 to 156 in SEQ ID NO: 3).

Generation of GAIL clade

The GAIL clade comprises GADE domain polypeptides of bacterial origin, having hexosaminidase, e.g., PNAG activity. This clade has not been described previously, and defines a cluster within the polypeptides of the invention. The clade is termed GAIL and polypeptides of this clade comprise Glyco_hydro_20 domain polypeptides of bacterial origin, and are in addition to having PNAG activity, characterized by comprising certain polypeptide motifs. The polypeptides of the domain comprise the motif example [GK]A[IL][IL][KSR][LQ]L, corresponding to positions 96 to 102 of SEQ ID NO: 3, where A and L (corresponding to positions 97 and 102 of SEQ ID NO: 3) are fully conserved in GAIL clade. Examples of polypeptides of the invention included in the clade are SEQ ID NO: 3 and SEQ ID NO: 9.

An alignment of the polypeptides of the invention is shown in FIG. 2. A phylogenetic tree of the polypeptides of the invention is shown in FIG. 1.

Example 8 Cleaning in Full-Scale Washing Machine

For wash performance testing in full scale washing machines, the P. fluorescens and S. aureus EPS extracts previously mentioned were spotted on 5×5 cm sterile textile swatches (WFK20A, 250 µl aliquots) and left to soak for 15 min at ambient temperature. The swatches were then attached to ballast tea towels and washed in Miele Laundry Washing Machines (Miele Softtronic, W2245) with and without enzyme, in liquid or powder detergent. The washes were run in tap water with 0.08 g/L iron(III) oxide nano-powder (544884; Sigma-Aldrich) in 4.6 g/L liquid detergent (Persil Universal gel) or with 0.7 g/L WFK 09V pigment soil (Wfk-Testgewebe GmbH, #00500) in 5.3 g/L powder model detergent T, respectively. The 30° C. Color program was used for these tests (run time 1 hour, 26 min). After washing, the items were line-dried at room temperature overnight. The remission ($REM^{460nm}$) values were measured using a Macbeth Color-Eye 7000 (CE7000), and are displayed in Tables 7 and 8. Wash performances ($\Delta REM(460\ nm) = REM^{460nm}_{(washed\ with\ enzyme)} - REM^{460nm}_{(washed\ without\ enzyme)}$) are also indicated.

TABLE 7

Cleaning of SEQ ID NO: 3 in full-scale washing machine in liquid detergent

| EPS spotted on T-shirt | Enzyme | Average Rem460 nm values | Wash performance (ΔRem460 nm) |
|---|---|---|---|
| P. fluorescens EPS, wfk20A | No enzyme | 47.4 | |
| P. fluorescens EPS, wfk20A | 0.2 µg/ml SEQ ID NO: 3 | 72.2 | 24.8 |
| S. aureus EPS, wfk20A | No enzyme | 41.2 | |
| S. aureus EPS, wfk20A | 0.2 ug/ml SEQ ID NO: 3 | 66.5 | 25.3 |

TABLE 8

Cleaning of SEQ ID NO: 3 in full-scale washing machine in powder model detergent T

| EPS spotted on T-shirt | Enzyme | Average Rem460 nm values | Wash performance (ΔRem460 nm) |
|---|---|---|---|
| P. fluorescens EPS, wfk20A | No enzyme | 58.6 | |
| P. fluorescens EPS, wfk20A | 0.2 ug/ml SEQ ID NO: 3 | 64.0 | 5.4 |
| S. aureus EPS, wfk20A | No enzyme | 60.2 | |
| S. aureus EPS, wfk20A | 0.2 ug/ml SEQ ID NO: 3 | 63.3 | 3.1 |

Example 9 Cleaning Properties of Hexosaminidase in Liquid Model Detergent on EPS from Different Microorganisms Crude extracts of biofilm extracellular polymeric substances (EPS) were prepared from S. aureus and P. fluorescens as described above. For wash performance testing, 50 ul aliquots of the crude EPS extracts were spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 3.33 g/L liquid model A detergent) and enzyme was added to each tube. 15 Washes without enzyme were included as controls. The test tubes were placed in a Stuart rotator and incubated for 1 hour at 37° C. at 20 rpm. The wash liquor was then removed, and the swatches were rinsed twice with 15° dH water and left to dry on filter paper overnight. The remission ($REM^{460nm}$) values were measured using a Macbeth Color-Eye 7000 (CE7000), and are displayed in table 9. Wash performances (4REM(460 nm)=$R^{460nm}_{(washed\ with\ enzyme)}$−$REM^{460nm}_{(washed\ without\ enzyme)}$) are also indicated.

Example 10 Biofilm Growth and Detachment Assay

Staphylococcus aureus 15981 was kindly provided by Iñigo Lasa (Valle et al., 2003, Mol Microbiol. 48(4):1075-87). The strain was grown on trypticase soy agar (TSA) at 37° C. overnight. Next day, a single colony was transferred to 15 ml trypticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L non-ionic detergent or 3.3 gr/L model A detergent (composition hard water and non-ionic and model A) containing 0 (control) or 20, 10, 2.5, 1.25, 0.62, 0.31, 0.16, 0.08, 0.04, 0.02 and 0.01

TABLE 9

Cleaning effects of Hexosaminidase with SEQ ID NO: 18 in liquid model detergent on EPS from different microorganisms

| | Enzyme | Enzyme concentration (µg/ml) | Average REM(460 nm) values | Wash performance (ΔREM(460 nm)) |
|---|---|---|---|---|
| Clean textile (wfk20A), no EPS | | 0 | 59.3 | |
| P. fluorescens EPS (wfk20A) | | 0 | 35.0 | |
| P. fluorescens EPS (wfk20A) | SEQ ID NO: 18 | 0.002 | 39.3 | 4.3 |
| P. fluorescens EPS (wfk20A) | SEQ ID NO: 18 | 0.02 | 51.4 | 16.4 |
| P. fluorescens EPS (wfk20A) | SEQ ID NO: 18 | 0.2 | 56.4 | 21.4 |
| S. aureus EPS (wfk20A) | | 0 | 34.7 | |
| S. aureus EPS (wfk20A) | SEQ ID NO: 18 | 0.002 | 45.5 | 10.5 |
| S. aureus EPS (wfk20A) | SEQ ID NO: 18 | 0.02 | 54.0 | 19.0 |
| S. aureus EPS (wfk20A) | SEQ ID NO: 18 | 0.2 | 56.7 | 21.7 |

μg/mL of dispersin SEQ ID NO: 18. After incubation at 37° C. for 1 hour, wells were washed with water and stained for 15 min with 100 μL of 0.095% crystal violet solution (SIGMA V5265). Wells were then rinsed twice with 100 μL water, dried and the plates were scanned.

The lowest concentration of each enzyme that could remove the visible formation of biofilm of the *S. aureus* 15981 organism after 1 hour incubation, in the presence and absence of detergent was determined (see Table 10). All enzymes were assayed per duplicate. The average of the minimal concentration of enzyme that removed the visible formation of *S. aureus* 15981 from the three assays is listed in Table 10.

TABLE 10

Minimal concentration of enzyme that can remove the visible formation of S. aureus 15981 after 1 hour incubation in either hard water or model A detergent

| Enzyme | Minimal concentration for biofilm removal in hard water μg/mL | Minimal concentration for biofilm removal in non-ionic detergent μg/mL | Minimal concentration for biofilm removal in model A detergent μg/mL |
|---|---|---|---|
| SEQ ID NO: 18 | 0.04 | 0.04 | 0.08 |

Example 11 Characterization of Dispersins

Dispersin Activity as a Function of pH

Activity assay: The activity of the dispersin having SEQ ID NO: 3 was measured with 4-Nitrophenyl N-acetyl-p-D-glucosaminide (4-NAG, CAS Number 3459-18-5, CHE00244) as substrate as a function of pH (4-10 in 1-unit increments). The concentrations of substrate and the dispersin having SEQ ID NO: 3 were 5 mM and 10.0 μM, respectively, in all measurements. The dilution buffers comprise: 50 mM MES (CAS Number: 4432-31-9), 50 mM glycine (CAS Number: 56-40-6), 50 mM acetic acid (CAS Number: 64-19-7) adjusted to pH4-10. The substrate solution (10 mM) was prepared by dissolving 34.23 mg 4-NAG in 10.0 mL water. Dissolution required rigorous vortex mixing and gentle heating. The enzyme concentration was determined by UV-Vis ($\varepsilon_{280}$=57890 M$^{-1}$cm$^{-1}$). The enzyme samples were incubated at the different pH-values in volumes of 200 μL in a thermomixer (in MTP) for 10 min and 500 rpm at 30° C. After 10 min, the MTP was incubated at 95° C. and 500 rpm for 10 min in thermomixer to end the reaction. Then the samples were transferred to ice bath and cooled for 2 min. The samples were added 20 μL 4 M NaOH to deprotonate pNP (induce yellow color). Absorbance at 405 nm was measured for 2 min in 10 sec. intervals. All measurements were produced in triplicates and reference samples were produced for all conditions (buffer instead of enzyme).

Results: The following table display the average absorbance (activity) subtracted the average absorbance of the reference samples measured after 10 min incubation at different pH values. In this case, the greatest activity is obtained at pH4.

Dispersin Activity as a Function of pH

| | pH | | | | | | |
|---|---|---|---|---|---|---|---|
| | 4 | 5 | 6 | 7 | 8 | 9 | 10 |
| $A_{405}$ | 0.50 | 0.43 | 0.31 | 0.29 | 0.30 | 0.32 | 0.37 |

Dispersin Stability as a Function of pH and NaCl

Stability assay—differential scanning fluorimetry: The thermal stability of the dispersin having SEQ ID NO: 3 was measured as a function of pH (4, 6, 7, 8, 10) and NaCl concentration (100, 200, and 300 mM). The thermal unfolding was monitored using intrinsic fluorescence utilizing a Prometheus NT.48. The concentrations the dispersin having SEQ ID NO: 3 was 0.2 mg/mL in all measurements. The enzyme concentration was determined by UV-Vis ($\varepsilon_{280}$=57890 M$^{-1}$cm$^{-1}$). The dilution buffers comprise: 50 mM MES (CAS Number: 4432-31-9), 50 mM glycine (CAS Number: 56-40-6), 50 mM acetic acid (CAS Number: 64-19-7) adjusted to pH4, 6, 7, 8, or The enzyme samples were prepared by mixing a 5 M NaCl stock, buffer, water (MQ), and enzyme to obtain the desired concentrations. The total volume of each mixture was 100 μL. The samples were loaded in the instrument in duplicates and measured from 20 to 95° C. with temperature ramping of 2.0° C./min.

Results: Melting temperatures ($T_m$-values) were derived from the thermograms using the PR. ThermControl v.2.0.4 software. The following table display the average $T_m$-values obtained at the different conditions:

| | | pH | | | | |
|---|---|---|---|---|---|---|
| | | 4 | 6 | 7 | 8 | 10 |
| [NaCl] mM | 0 | 52.1 | 52.9 | 51.1 | 50.0 | 29.2 |
| | 100 | 50.0 | 52.3 | 50.1 | 48.5 | N/A |
| | 200 | 49.1 | 51.9 | 49.6 | 47.8 | N/A |
| | 300 | 48.3 | 51.4 | 48.8 | 46.9 | N/A |

Dispersin Activity as a Function of Temperature

Activity assay: The activity of the dispersin having SEQ ID NO: 3 was measured with 4-Nitrophenyl N-acetyl-p-D-glucosaminide (4-NAG, CAS Number 3459-18-5, CHE00244) as substrate at pH7. The concentrations of substrate and the dispersin having SEQ ID NO: 3 were 1 mM and 5 μM, respectively, in all measurements. The dilution buffer comprises: 50 mM MES (CAS Number: 4432-31-9), 50 mM glycine (CAS Number: 56-40-6), 50 mM acetic acid (CAS Number: 64-19-7), pH7.

The substrate solution (10 mM) was prepared by dissolving 35.9 mg 4-NAG in 10.482 mL water. Dissolution required rigorous vortex mixing and gentle heating. The enzyme concentration was determined by UV-Vis ($\varepsilon_{280}$=57890 M$^{-1}$cm$^{-1}$). The reaction mixture comprised 23.7 μL enzyme (42.3 μM), 20 μL substrate, and 156.3 μL buffer.

The enzyme samples were incubated in volumes of 200 μL in a thermomixer for 10 min and 500 rpm at 20, 30, 40, 45, 50, 55, 60, or 70° C. After 10 min, the samples were transferred to ice bath and cooled for 2 min. The samples were added 10 μL 4 M NaOH to deprotonate pNP (induce yellow color). 180 μL reaction mixture was transferred to a MT plate and absorbance at 405 nm was measured for 1 min in 10 sec. intervals. All measurements were produced in duplicates and reference samples were produced for all conditions (buffer instead of enzyme).

Results: The following table displays the average absorbance (activity) subtracted the average absorbance of the reference samples measured after 10 min incubation at different temperatures. The results demonstrate that the activity increases with increasing temperature until 50° C. Hereafter, the activity rapidly decreases with temperature.

Dispersin Activity as a Function of Temperature

| | 20° C. | 30° C. | 40° C. | 45° C. | 50° C. | 55° C. | 60° C. | 70° C. |
|---|---|---|---|---|---|---|---|---|
| $A_{405}$ | 0.00 | 0.02 | 0.02 | 0.03 | 0.03 | 0.01 | 0.01 | 0.00 |

What is claimed is:

1. A method of treating a fabric, comprising contacting the fabric with an aqueous solution of a hexosaminidase having β-1,6 N-acetylglucosaminidase activity, wherein the fabric comprises a biofilm comprising polymers of N-acetyl-glucosamine (PNAG), wherein
   (a) the amino acid sequence of the hexosaminidase has at least 90% sequence identity to the amino acid sequence of SEQ ID NO: 18, and
   (b) the biofilm is reduced or removed from the fabric.

2. The method of claim 1, wherein the hexosaminidase comprises one or more of the following motifs: GXDE, wherein X is any naturally-occurring amino acid, [EQ][NRSHA][YVFL][AGSTC][IVLF][EAQYN][SN], [VLIM][LIV]G[GAV]DE[VI][PSA] or [GK]A[IL][IL][KSR][LQ]L.

3. The method of claim 1, wherein the amino acid sequence of the hexosaminidase has at least 95% sequence identity to the amino acid sequence of SEQ ID NO: 18.

4. The method of claim 1, wherein the amino acid sequence of the hexosaminidase has at least 96% sequence identity to the amino acid sequence of SEQ ID NO: 18.

5. The method of claim 1, wherein the amino acid sequence of the hexosaminidase has at least 97% sequence identity to the amino acid sequence of SEQ ID NO: 18.

6. The method of claim 1, wherein the amino acid sequence of the hexosaminidase has at least 98% sequence identity to the amino acid sequence of SEQ ID NO: 18.

7. The method of claim 1, wherein the amino acid sequence of the hexosaminidase has at least 99% sequence identity to the amino acid sequence of SEQ ID NO: 18.

8. The method of claim 1, wherein the hexosaminidase comprises the amino acid sequence of SEQ ID NO: 18.

9. The method of claim 1, further comprising rinsing and drying the fabric.

10. A method for cleaning or laundering a fabric, comprising
    (a) exposing the fabric to a wash liquor comprising a detergent composition comprising a hexosaminidase having β-1,6 N-acetylglucosaminidase activity, wherein the amino acid sequence of the hexosaminidase has at least 90% sequence identity to the amino acid sequence of SEQ ID NO: 18, and wherein the fabric comprises a biofilm comprising polymers of N-acetyl-glucosamine (PNAG); and
    (b) completing at least one wash cycle;
    wherein the biofilm is reduced or removed from the fabric.

11. The method of claim 10, wherein the hexosaminidase comprises one or more of the following motifs: GXDE, wherein X is any naturally-occurring amino acid, [EQ][NRSHA][YVFL][AGSTC][IVLF][EAQYN][SN], [VLIM][LIV]G[GAV]DE[VI][PSA], or [GK]A[IL][IL][KSR][LQ]L.

12. The method of claim 10, wherein the amino acid sequence of the hexosaminidase has at least 95% sequence identity to the amino acid sequence of SEQ ID NO: 18.

13. The method of claim 10, wherein the amino acid sequence of the hexosaminidase has at least 96% sequence identity to the amino acid sequence of SEQ ID NO: 18.

14. The method of claim 10, wherein the amino acid sequence of the hexosaminidase has at least 97% sequence identity to the amino acid sequence of SEQ ID NO: 18.

15. The method of claim 10, wherein the amino acid sequence of the hexosaminidase has at least 98% sequence identity to the amino acid sequence of SEQ ID NO: 18.

16. The method of claim 10, wherein the amino acid sequence of the hexosaminidase has at least 99% sequence identity to the amino acid sequence of SEQ ID NO: 18.

17. The method of claim 10, wherein the hexosaminidase comprises the amino acid sequence of SEQ ID NO: 18.

18. The method of claim 10, further comprising rinsing and drying the fabric.

19. The method of claim 10, wherein the hexosaminidase is present in the detergent composition in an amount of 0.01 to 100 mg/mL.

\* \* \* \* \*

SEQUENCE LISTING

```
Sequence total quantity: 32
SEQ ID NO: 1             moltype = DNA  length = 1086
FEATURE                  Location/Qualifiers
sig_peptide              1..90
mat_peptide              91..1083
source                   1..1086
                         mol_type = genomic DNA
                         organism = Lactobacillus paraplantarum
CDS                      1..1083
SEQUENCE: 1
atgaagtacc gacattactt tacacaacta ttaatattta ttagcccgct gattcttctt    60
tgcttcagcc agccccgtac ggcaactgcc aattcatcaa cattgaatac tagtcaaggg   120
gtcatgttag atttaggccg ccatccgtta gatgaaactg caattaaagc cgtcattagt   180
gctgctgccg aacaacacat gcaatacgtc gaactacact tatcagataa cgaacatcta   240
tgctttcaat cggcttattt aggtaatgcc gcatcggcaa ccgtattatc ggcgacgact   300
ttagaacagc tagttgctta tgccaatcag ttgaacattg aactagttcc tgatgttgac   360
cttccctcgc acgcgggagc cattttacgc caattgcaac aaactcatcc cgatatttac   420
aataccgtta agttggatga cgaaaccatc gactatacta accggcagc aatcagtctc    480
gctaccacac tttatggcga gctcgatgct agttttaaca atcaaagcca gcacgatttg   540
atgctcggcg ctgatgaggt tcctggcagc gctagcgcct atatcgaact gaccaccttt   600
atcaatcagg tcagtcgatt tcaaaatcaa cacggcttca acactagtat ttggaatgat   660
tcgctattaa aaaatgaact cactcgtctg gattcaaaca ttacaatcaa ttactggtca   720
caatctggta acaataccga tgtggctatc attgccgacc gctatgccaa ccgtgtatcc   780
gttcccgaca ttttagcctc tgggcatccg atcgtgaact gtaatagtta tgcgacctat   840
tatcaaatca aaaatattgg caatgtcaat gatgacgatt actttattaa ttatcttaat   900
cacacctttc gcccgaatat ctttaacgaa attgacacca tgggcataa tcaggattgg   960
accattgaag atggcgtcac aactaacggt atcttagtta gcttgtgggg ggccgattca  1020
gagcatgtta caccaactgc catcgtcaat ttcattaaac gtatgacgat tccacggtca  1080
ttttaa                                                             1086

SEQ ID NO: 2             moltype = AA  length = 361
FEATURE                  Location/Qualifiers
source                   1..361
                         mol_type = protein
                         organism = Lactobacillus paraplantarum
SEQUENCE: 2
MKYRHYFTQL LIFISPLILL CFSQPRTATA NSSTLNTSQG VMLDLGRHPL DETAIKAVIS    60
AAAEQHMQYV ELHLSDNEHL CFQSAYLGNA ASATVLSATT LEQLVAYANQ LNIELVPDVD   120
LPSHAGAILR QLQQTHPDIY NTVKLDDETI DYTKPAAISL ATTLYGELDA SFNNQSQHDL   180
MLGADEVPGS ASAYIELTTF INQVSRFQNQ HGFNTSIWND SLLKNELTRL DSNITINYWS   240
QSGNNTDVAI IADRYANRVS VPDILASGHP IVNCNSYATY YQIKNIGNVN DDDYFINYLN   300
HTFRPNIFNE IDTNGHNQDW TIEDGVTTNG ILVSLWGADS EHVTPTAIVN FIKRMTIPRS   360
F                                                                  361

SEQ ID NO: 3             moltype = AA  length = 331
FEATURE                  Location/Qualifiers
source                   1..331
                         mol_type = protein
                         organism = Lactobacillus paraplantarum
SEQUENCE: 3
NSSTLNTSQG VMLDLGRHPL DETAIKAVIS AAAEQHMQYV ELHLSDNEHL CFQSAYLGNA    60
ASATVLSATT LEQLVAYANQ LNIELVPDVD LPSHAGAILR QLQQTHPDIY NTVKLDDETI   120
DYTKPAAISL ATTLYGELDA SFNNQSQHDL MLGADEVPGS ASAYIELTTF INQVSRFQNQ   180
HGFNTSIWND SLLKNELTRL DSNITINYWS QSGNNTDVAI IADRYANRVS VPDILASGHP   240
IVNCNSYATY YQIKNIGNVN DDDYFINYLN HTFRPNIFNE IDTNGHNQDW TIEDGVTTNG   300
ILVSLWGADS EHVTPTAIVN FIKRMTIPRS F                                  331

SEQ ID NO: 4             moltype = DNA  length = 1146
FEATURE                  Location/Qualifiers
sig_peptide              1..84
mat_peptide              85..1143
```

-continued

| | | |
|---|---|---|
| source | 1..1146 | |
| | mol_type = genomic DNA | |
| | organism = Lactobacillus apinorum | |
| CDS | 1..1143 | |

SEQUENCE: 4

```
atgagaaata aacgattat aatcgttgga atgatattgt ttttagtctt aatgtttata    60
caattaggca gttagcgaa aaagacactt gccgataca gtaacgatac caaaagaatt   120
ggtctatcat tagattgttc cagaacatat tattctcctt ctacaatcaa aaagtatata   180
gatttattaa agaaagatca tggtacatat cttcaattac acttaaatga caatgaaaga   240
tatggtgttg aaagttcaac gttaggacaa acaacgcaaa acgctacact taaagatggt   300
gtttattaca ataataaaac acacttagca ttttaagta aaaatcaatt attagatgta   360
attcaatacg gttacactca tggaattgaa gtaattccag aaatagactt acctggacat   420
gctcaatcta tattaagct tctttcatat acttcagaag gaaagtaaact agttaaagag   480
ttagaaaaata aagtagtta caatgaaatg tactacaaca aacaagctac gattgattt    540
tcaaaaaagc ttttaagtga atatgttggc atgcttccca gtggataca cattattgta   600
ggtgccgatg aaataactat tagtgataaa agtgatcaag aagccgttgt taagtatatt   660
aatgccattg atgattatgt taatgctaat catttaaac ttgaaatgtg aatgatagt    720
tttcataagg cggttttaag taaatatcat aaagtatt taattaatta ctggagttta   780
acaggtgaag ttagctcaag taaggataga aaagacaaca tcaggatgag agcaacactt   840
cctgaattaa ataaggctgg ttttaagaca attaactaca atagttatta tctatatatg   900
attacagatc caacatcatt taccaatgaa tctaagaaaa tttggacttc cgagtttaaa   960
aaatgggaaaa tgaatatgtg gaatgatgaa tctacaaaag atatcacaaa gagcgccaat  1020
aatattggtg ctgccatatc aatatggggt gaatatccaa atcaatatac tggtgatcaa  1080
acatataata agacatatta ttacgttgat acgttttaa aggcccagga taaatttact  1140
aagtaa                                                              1146
```

| | | |
|---|---|---|
| SEQ ID NO: 5 | moltype = AA   length = 381 | |
| FEATURE | Location/Qualifiers | |
| source | 1..381 | |
| | mol_type = protein | |
| | organism = Lactobacillus apinorum | |

SEQUENCE: 5

```
MRNKRFIIVG MILFLVLMFI QLGSLAKKTL ADTSNDTKRI GLSLDCSRTY YSPSTIKKYI    60
DLLKKDHGTY LQLHLNDNER YGVESSTLGQ TTQNATLKDG VYYNNKTHLA FLSKNQLLDV   120
IQYGYTHGIE VIPEIDLPGH AQSIFKLLSY TSEGKKLVKE LENKDGYNEM YYNKQATIDF   180
SKKLLSEYVG MLPSGYHIIV GADEITISDK SDQEAVVKYI NAIDDYVNAN HLKLEMWNDS   240
FHKAVLSKYH KDILINYWSL TGEVSSSKDR KDNIRMRATL PELNKAGFKT INYNSYYLYM   300
ITDPTSFTNE SKKIWTSEFK KWKMNMWNDE STKDITKSAN NIGAAISIWG EYPNQYTGDQ   360
TYNKTYYYVD TFLKAQDKFT K                                             381
```

| | | |
|---|---|---|
| SEQ ID NO: 6 | moltype = AA   length = 353 | |
| FEATURE | Location/Qualifiers | |
| source | 1..353 | |
| | mol_type = protein | |
| | organism = Lactobacillus apinorum | |

SEQUENCE: 6

```
TLADTSNDTK RIGLSLDCSR TYYSPSTIKK YIDLLKKDHG TYLQLHLNDN ERYGVESSTL    60
GQTTQNATLK DGVYYNNKTH LAFLSKNQLL DVIQYGYTHG IEVIPEIDLP GHAQSIFKLL   120
SYTSEGKKLV KELENKDGYN EMYYNKQATI DFSKKLLSEY VGMLPSGYHI IVGADEITIS   180
DKSDQEAVVK YINAIDDYVN ANHLKLEMWN DSFHKAVLSK YHKDILINYW SLTGEVSSSK   240
DRKDNIRMRA TLPELNKAGF KTINYNSYYL YMITDPTSFT NESKKIWTSE FKKWKMNMWN   300
DESTKDITKS ANNIGAAISI WGEYPNQYTG DQTYNKTYYY VDTFLKAQDK FTK           353
```

| | | |
|---|---|---|
| SEQ ID NO: 7 | moltype = DNA   length = 1086 | |
| FEATURE | Location/Qualifiers | |
| sig_peptide | 1..90 | |
| mat_peptide | 91..1083 | |
| source | 1..1086 | |
| | mol_type = genomic DNA | |
| | organism = Lactobacillus paraplantarum | |
| CDS | 1..1083 | |

SEQUENCE: 7

```
atgaagtgcc gacattactt tacacaacta ttaatattta ttagcccgct gattcttctt    60
tgcttcagcc agccccgtac ggcaactgcc aattcatcaa cattgaatac tagtcaaggg   120
gtcatgttag atttaggtcg ccatccgtta gatgaaactg caattaaagc cgtcattagt   180
gctgctgccg aacaacacat gcaatacgtc gaactacact tatcagataa cgaacatcta   240
tgctttcaat cggcttattt aggtaatgcc gcatcggcaa ccgtattatc ggcaacgact   300
ttagaacagc tagttgctta tgccaatcag ttgaacattg aactagttcc tgatgttgac   360
cttccctcgc acgcgggagc catttttacgc caattgcaac aaactcatcc cgatatttac   420
aataccgtta agttggatga cgaaaccatc gactatacta aaccggcagc agtcagtctc   480
gctaccacac tttatggcga gctcgatgct agttttaaca atcaaagcca gcacgatttg   540
atgctcggcg ctgatgaggt ttctggcagc gctagcgcct atatcgaact gaccacctttt   600
atcaatcagg tcagtcgatt tcaaaatcaa aacggcttca cactagtat ttggaatgat   660
tcgctattaa aaaatgaact tcgtctg gattcaaaca ttacaatcaa ttactggtca   720
caatctggta acaataccga tgcggcatc attgccgacc gctatgcaa ccgtgcatcc   780
gttcccgaca ttttagcctc tgggcatccg atcgtgaact gtaatagtta tgcgacctat   840
tatcaattca aaaatattgg caatgtcaat gatgacaatt actttattaa ttatcttaat   900
cacacccttt gcccgaatat ctttaacgaa attgacacca acgggcataa tcaggattgg  960
accattgaag atggcgtcac aactaacggt atcttagtta gcttgtgggg ggccgattca  1020
```

```
gagcatgtta caccaactgc tattgtcaat tcattaaac gtatggcgat tccccggtca    1080
ttttaa                                                               1086

SEQ ID NO: 8            moltype = AA  length = 361
FEATURE                 Location/Qualifiers
source                  1..361
                        mol_type = protein
                        organism = Lactobacillus paraplantarum
SEQUENCE: 8
MKCRHYFTQL LIFISPLILL CFSQPRTATA NSSTLNTSQG VMLDLGRHPL DETAIKAVIS    60
AAAEQHMQYV ELHLSDNEHL CFQSAYLGNA ASATVLSATT LEQLVAYANQ LNIELVPDVD    120
LPSHAGAILR QLQQTHPDIY NTVKLDDETI DYTKPAAVSL ATTLYGELDA SFNNQSQHDL    180
MLGADEVSGS ASAYIELTTF INQVSRFQNQ NGFNTSIWND SLLKNELNRL DSNITINYWS    240
QSGNNTDAAI IADRYANRAS VPDILASGHP IVNCNSYATY YQFKNIGNVN DDNYFINYLN    300
HTFRPNIFNE IDTNGHNQDW TIEDGVTTNG ILVSLWGADS EHVTPTAIVN FIKRMAIPRS    360
F                                                                    361

SEQ ID NO: 9            moltype = AA  length = 331
FEATURE                 Location/Qualifiers
source                  1..331
                        mol_type = protein
                        organism = Lactobacillus paraplantarum
SEQUENCE: 9
NSSTLNTSQG VMLDLGRHPL DETAIKAVIS AAAEQHMQYV ELHLSDNEHL CFQSAYLGNA    60
ASATVLSATT LEQLVAYANQ LNIELVPDVD LPSHAGAILR QLQQTHPDIY NTVKLDDETI    120
DYTKPAAVSL ATTLYGELDA SFNNQSQHDL MLGADEVSGS ASAYIELTTF INQVSRFQNQ    180
NGFNTSIWND SLLKNELNRL DSNITINYWS QSGNNTDAAI IADRYANRAS VPDILASGHP    240
IVNCNSYATY YQFKNIGNVN DDNYFINYLN HTFRPNIFNE IDTNGHNQDW TIEDGVTTNG    300
ILVSLWGADS EHVTPTAIVN FIKRMAIPRS F                                   331

SEQ ID NO: 10           moltype = AA  length = 27
FEATURE                 Location/Qualifiers
REGION                  1..27
                        note = Signal peptide
source                  1..27
                        mol_type = protein
                        organism = synthetic construct
SEQUENCE: 10
MKKPLGKIVA STALLISVAF SSSIASA                                        27

SEQ ID NO: 11           moltype = AA  length = 8
FEATURE                 Location/Qualifiers
source                  1..8
                        mol_type = protein
                        organism = synthetic construct
SEQUENCE: 11
HHHHHHPR                                                             8

SEQ ID NO: 12           moltype =     length =
SEQUENCE: 12
000

SEQ ID NO: 13           moltype =     length =
SEQUENCE: 13
000

SEQ ID NO: 14           moltype =     length =
SEQUENCE: 14
000

SEQ ID NO: 15           moltype =     length =
SEQUENCE: 15
000

SEQ ID NO: 16           moltype = DNA  length = 1557
FEATURE                 Location/Qualifiers
sig_peptide             1..75
mat_peptide             76..1521
source                  1..1557
                        mol_type = genomic DNA
                        organism = Strepotcocus merionis
CDS                     1..1521
variation               347
                        note = N=A, C, G or T
variation               351
                        note = N=A, C, G or T
variation               357
                        note = N=A, C, G or T
variation               372
```

```
                        note = N=A, C, G or T
SEQUENCE: 16
atgcataagg ttaaggtact tttagggacg gttctgctct ttttaacact attgttgaca    60
ggacagccag aggcacaaga acctatcgtt aaactctcag gcggagtgat ggtggatgtg   120
gctaggagat attactctct aaactctctg aaatctatca ttgatactgt ttcggagaat   180
aaaggagact ttgttcatct ccacttgaca gatgatcaaa attatgggtt ggagagtcag   240
tttctcaatc aaacagcttc aaatgcaata tataatcaag atgatcaaag ctatactaat   300
cctaatacga atcgaaaatt tctcagttat ggacagsrty rthrasnras nthrasnarg   360
yshsrtyrgy gnttggctga gcttaaaagt tatgcgggtt caaaaggcat ccgattgata   420
ccagaaattg acaccccagc tcatacagga gggctaaagg ccttgcttcc ctacgcgag    480
ccagcagtta ctagtcaatt taagtgggta tcttgggacg aagataggca actagatctt   540
gatgcagcta ctactcagga agctgttaga cagttatata tggaactagt ccagaattg    600
cctggcttag agtatatcca tattggaggc gatgaaattt ctggaggact tatacaaggc   660
cagtcttca ttagtcatgt gaatcagtta tgcgactatt tagcaggtca aggtatcaaa   720
actcaaatat ggaatgatag cttatcccgt caactgctac cttctttaaa tcgtaacgtt   780
gagattgctt attgggggta tcttcctcac agaaatccag atttagcaac agcttctgac   840
cttagtgatc aggatttaa gctccttaat tataatgggt attatctagc ttttgttcct   900
aagccctcag aaaaacttca atcggatgcc ctatttgcaa caatgatat tctaaagact   960
tggaatcttt cccagtttca tatggatacg ggtgattcca ttaatagttt aaagaatgtc  1020
attggagcgg cttttccat atggagtgaa gagtcagctg gtctgactga cgaggagata   1080
tttctgcca tgggtagtcc gattcgagct cttttgacag ttatcaatca agaaatata   1140
aagagaaacg agaatacgac aactaccacc accgagtcga tgactgaggc tacgacaact  1200
attacaactg agccgacaac ccaatcaacc acagaaagta cgacaactac tacaaccgag  1260
tcaacgacag agactacgac aactgtcaca actgagtcaa caactaagtc gaccacagaa  1320
ggcacgacag aaacaacaac ccctatccca ccaatgcctc agcctacaac gtctcctgag  1380
acaagtacag ctacacatgc aacaacgact aacccaagta catcaaaaga tggcaataaa  1440
ctgtctaaat caaaacggat attgccaagt acaggtgaaa cgattggtgt cctttcagta  1500
gcaggattgg cgctcttctt gtttgttggg cttacatatt accgtcacaa gaagaat    1557

SEQ ID NO: 17           moltype = AA  length = 507
FEATURE                 Location/Qualifiers
source                  1..507
                        mol_type = protein
                        organism = Strepotcocus merionis
VARIANT                 113
                        note = X=G, D, R or H
VARIANT                 114
                        note = X=R, H, C or Y
VARIANT                 115
                        note = X=R, K or Q
VARIANT                 116
                        note = X=E, G, A, V, Q, R, P or L
VARIANT                 117
                        note = X=R, S or T
VARIANT                 118
                        note = X=S or L
VARIANT                 119
                        note = X=R, S, or T
VARIANT                 120
                        note = X=R or K
VARIANT                 121
                        note = X=R, P, C or S
VARIANT                 122
                        note = X=G, D, R or H
VARIANT                 123
                        note = X=R, Q or W
VARIANT                 124
                        note = X=R, W or C
SEQUENCE: 17
MHKVKVLLGT VLLFLTLLLT GQPEAQEPIV KLSGGVMVDV ARRYYSLNSL KSIIDTVSEN    60
KGDFVHLHLT DDQNYGLESQ FLNQTASNAI YNQDDQSYTN PNTNRKFLSY GQXXXXXXXX   120
XXXXLAELKS YAGSKGIRLI PEIDTPAHTG GLKALLPYAE PAVTSQFKWV SWDEDRQLDL   180
DAATTQEAVR QLYMELVREL PGLEYIHIGG DEISGGLIQG QSFISHVNQL CDYLAGQGIK   240
TQIWNDSLSR QLLPSLNRNV EIAYWGYLPH RNPDLATASD LSDQDFKLLN YNGYYLAFVP   300
KPSEKLQSDA LFAANDILKT WNLSQFHMDT GDSINSLKNV IGAAFSIWSE ESAGLTDEEI   360
FSAMGSPIRA LLTVINQENI KRNETTTTT ESMTEATTT ITTEPTTQST TESTTTTTE    420
STTETTTVT TESTTKSTTE GTTETTTPIP PMPQPTTSPE TSTATHATTT NPSTSKDGNK   480
LSKSKRILPS TGETIGVLSV AGLALFL                                      507

SEQ ID NO: 18           moltype = AA  length = 491
FEATURE                 Location/Qualifiers
source                  1..491
                        mol_type = protein
                        organism = Steptococcus merionis
SEQUENCE: 18
MHKVKVLLGT VLLFLTLLLT GQPEAQEPIV KLSGGVMVDV ARRYYSLNSL KSIIDTVSEN    60
KGDFVHLHLT DDQNYGLESQ FLNQTASNAI YNQDDQSYTN PNTNRKFLSY GQLAELKSYA   120
GSKGIRLIPE IDTPAHTGGL KALLPYAEPA VTSQFKWVSW DEDRQLDLDA ATTQEAVRQL   180
YMELVRELPG LEYIHIGGDE ISGGLIQGQS FISHVNQLCD YLAGQGIKTQ IWNDSLSRQL   240
```

```
LPSLNRNVEI AYWGYLPHRN PDLATASDLS DQDFKLLNYN GYYLAFVPKP SEKLQSDALF    300
AANDILKTWN LSQFHMDTGD SINSLKNVIG AAFSIWSEES AGLTDEEIFS AMGSPIRALL    360
TVINQENIAT TTITTEPTTQ STTESTTTTT TESTTETTTT VTTESTTKST TEGTTETTTP    420
IPPMPQPTTS PETSTATHAT TTNPSTSKDG NKLSKSKRIL PSTGETIGVL SVAGLALFLF    480
VGLTYYRHKK N                                                        491

SEQ ID NO: 19               moltype = AA  length = 482
FEATURE                     Location/Qualifiers
source                      1..482
                            mol_type = protein
                            organism = Streptococcus merionis
SEQUENCE: 19
QEPIVKLSGG VMVDVARRYY SLNSLKSIID TVSENKGDFV HLHLTDDQNY GLESQFLNQT     60
ASNAIYNQDD QSYTNPNTNR KFLSYGQLAE LKSYAGSKGI RLIPEIDTPA HTGGLKALLP    120
YAEPAVTSQF KWVSWDEDRQ LDLDAATTQE AVRQLYMELV RELPGLEYIH IGGDEISGGL    180
IQGQSFISHV NQLCDYLAGQ GIKTQIWNDS LSRQLLPSLN RNVEIAYWGY LPHRNPDLAT    240
ASDLSDQDFK LLNYNGYYLA FVPKPSEKLQ SDALFAANDI LKTWNLSQFH MDTGDSINSL    300
KNVIGAAFSI WSEESAGLTD EEIFSAMGSP IRALLTVINQ ENIKRNENTT TTTTESMTEA    360
TTTITTEPTT QSTTESTTTT TTESTTETTT VTTESTTKS  TTEGTTETTT PIPPMPQPTT    420
SPETSTATHA TTTNPSTSKD GNKLSKSKRI LPSTGETIGV LSVAGLALFL FVGLTYYRHK    480
KN                                                                  482

SEQ ID NO: 20               moltype = AA  length = 11
FEATURE                     Location/Qualifiers
source                      1..11
                            mol_type = protein
                            organism = synthetic construct
SEQUENCE: 20
LEGLYALATY R                                                         11

SEQ ID NO: 21               moltype = AA  length = 12
FEATURE                     Location/Qualifiers
source                      1..12
                            mol_type = protein
                            organism = synthetic construct
SEQUENCE: 21
PHEGLYALAT YR                                                        12

SEQ ID NO: 22               moltype = AA  length = 12
FEATURE                     Location/Qualifiers
source                      1..12
                            mol_type = protein
                            organism = synthetic construct
SEQUENCE: 22
TYRGLYALAT YR                                                        12

SEQ ID NO: 23               moltype = AA  length = 11
FEATURE                     Location/Qualifiers
source                      1..11
                            mol_type = protein
                            organism = synthetic construct
SEQUENCE: 23
PHEGLYALAL E                                                         11

SEQ ID NO: 24               moltype = AA  length = 12
FEATURE                     Location/Qualifiers
source                      1..12
                            mol_type = protein
                            organism = synthetic construct
SEQUENCE: 24
PHEGLYALAP HE                                                        12

SEQ ID NO: 25               moltype = AA  length = 12
FEATURE                     Location/Qualifiers
source                      1..12
                            mol_type = protein
                            organism = synthetic construct
SEQUENCE: 25
PHEGLYVALT YR                                                        12

SEQ ID NO: 26               moltype = AA  length = 12
FEATURE                     Location/Qualifiers
source                      1..12
                            mol_type = protein
                            organism = synthetic construct
SEQUENCE: 26
PHEGLYALAM ET                                                        12

SEQ ID NO: 27               moltype = AA  length = 11
```

```
FEATURE                 Location/Qualifiers
source                  1..11
                        mol_type = protein
                        organism = synthetic construct
SEQUENCE: 27
TRPLEVALTY R                                                                    11

SEQ ID NO: 28           moltype = AA  length = 11
FEATURE                 Location/Qualifiers
source                  1..11
                        mol_type = protein
                        organism = synthetic construct
SEQUENCE: 28
PHEGLYALAL E                                                                    11

SEQ ID NO: 29           moltype = AA  length = 12
FEATURE                 Location/Qualifiers
source                  1..12
                        mol_type = protein
                        organism = synthetic construct
SEQUENCE: 29
PHEGLYALAP HE                                                                   12

SEQ ID NO: 30           moltype = AA  length = 11
FEATURE                 Location/Qualifiers
source                  1..11
                        mol_type = protein
                        organism = synthetic construct
SEQUENCE: 30
PHEGLYALAL E                                                                    11

SEQ ID NO: 31           moltype = AA  length = 11
FEATURE                 Location/Qualifiers
source                  1..11
                        mol_type = protein
                        organism = synthetic construct
SEQUENCE: 31
PHEGLYALAL E                                                                    11

SEQ ID NO: 32           moltype = AA  length = 10
FEATURE                 Location/Qualifiers
source                  1..10
                        mol_type = protein
                        organism = synthetic construct
SEQUENCE: 32
LEGLYALALE                                                                      10
```